United States Patent
Willoughby et al.

(10) Patent No.: US 9,701,633 B2
(45) Date of Patent: Jul. 11, 2017

(54) METHODS AND INTERMEDIATES USEFUL FOR THE PREPARATION OF ALPHA-BRANCHED ARYL PHTHALIMIDES AND ALPHA-BRANCHED ARYL AMINES

(71) Applicant: Ripon College, Ripon, WI (US)

(72) Inventors: Patrick H. Willoughby, Ripon, WI (US); Robert N. Enright, Ripon, WI (US); Lucas T. Henningsen, Ripon, WI (US); Lincoln I. Wurtz, Ripon, WI (US); Emily R. Cliff, Ripon, WI (US); Jeffrey L. Grinde, Ripon, WI (US)

(73) Assignee: RIPON COLLEGE, Ripon, WI (US)

( * ) Notice: Subject to any disclaimer, the term of this patent is extended or adjusted under 35 U.S.C. 154(b) by 0 days.

(21) Appl. No.: 14/989,628

(22) Filed: Jan. 6, 2016

(65) Prior Publication Data

US 2016/0200680 A1   Jul. 14, 2016

Related U.S. Application Data

(60) Provisional application No. 62/101,277, filed on Jan. 8, 2015.

(51) Int. Cl.
*C07D 209/50* (2006.01)

(52) U.S. Cl.
CPC .................. *C07D 209/50* (2013.01)

(58) Field of Classification Search
CPC .................................................. C07D 209/50
See application file for complete search history.

(56) References Cited

U.S. PATENT DOCUMENTS 4,121,369 A * 10/1978 Lopez .................. A01K 87/002
                                                              43/18.1 R

OTHER PUBLICATIONS

Hadfield et al. "Imide and isatin derivatives as γ-lactam mimics of β-lactam antibiotics" Arkivoc 2002, 6, 125-144.*

Kaupp et al. "Organic gas-solid reactions. Additions of hydrogen halides to N-vinylphthalimide and substitutions of its hydrate" Chem. Ber. 1986, 119, 2387-2392.*
Bryan, W. M. "An Improved Preparation of Benzhydrylamine" J. Org. Chem. 1986, 51, 3371-3372.*
Gnichtel, H. "Preparation of α-amino ketoximes by hydrazinolysis of α-phthaloylamino ketoximes" Chem. Ber. 1965, 98, 567-575.*
Enright, et al., "Mechanistic studies into the reaction of aldehydes with N-acylphthalimides", The 249th ACS National Meeting, Denver, CO. USA, Mar. 22-26, 2015.
Grinde, et al., "Phthalimide-catalyzed reaction of aldehydes with N-acylphthalimides", The 251st ACS National Meeting & Exposition, San Diego, CA, United States, Mar. 13-17, 2016.
Henningsen, et al., "Lithium-promoted reaction of aldehydes with N-acylphthalimides", The 249th ACS National Meeting, Denver, CO. USA, Mar. 22-26, 2015.
Lee, et al., "Synthesis of 5,6-dihydrophenanthridines via N,O-acetal TMS ethers", Tetrahedron Letters 54, 5167-5171 (2013).
Liu, et al., "BF3•Et2O catalyzed diastereoselective nucleophilic reactions of 3-silyloxypiperidine N,O-acetal with silyl enol ether and application to the asymmetric synthesis of (+)-febrifugine", Tetrahedron Letters, vol. 50, 4046-4049 (2009).
Onomura, et al., "Mannich-Type Reaction of N,O-Acetals with Ketones Mediated by a Combination of TiCl4 and PhSiCl3", Heterocycles, 82(1), pp. 325-332; 2010.
Paeth, et al., "Lithium-mediated reaction of N-acylimides with aldehydes: Expanding the scope to include electron-rich aldehydes", The 251st ACS National Meeting & Exposition, San Diego, CA, United States, Mar. 13-17, 2016.
Renaud, et al., "Stereoselectivity of the reactions of N-phthaloyl iminium ions and amino-substituted radicals derived from threonine", Tetrahedron Letters, vol. 37 (15), 2569-2572 (1996).
Stojanovic, et al., "Stereoselective Reactions of Phthalimido-Substituted Radicals Derived from (±)-Threonine: A comparison with reactions of N-phthaloyliminium ions", Helvetica Chimica Acta vol. 81, 268-284 (1998).
Willoughby, et al., "Synthesis of N-Phthalimido-O-Acyl-N,O-Acetals from Aldehydes and Their Conversion into Branched Phthalimides", The 249th ACS National Meeting, Denver, CO. USA, Mar. 22-26, 2015.

* cited by examiner

*Primary Examiner* — Michael Barker
*Assistant Examiner* — Amanda L Aguirre
(74) *Attorney, Agent, or Firm* — Viksnins Harris & Padys PLLP

(57) ABSTRACT

The invention provides methods and intermediates that are useful for preparing α-branched aryl phthalimides and α-branched aryl amines.

18 Claims, No Drawings

METHODS AND INTERMEDIATES USEFUL FOR THE PREPARATION OF ALPHA-BRANCHED ARYL PHTHALIMIDES AND ALPHA-BRANCHED ARYL AMINES

PRIORITY OF INVENTION

This application claims priority to U.S. Provisional Application No. 62/101,277, filed on 8 Jan. 2015. The entire content of U.S. Provisional Application No. 62/101,277 is incorporated herein by reference.

BACKGROUND

Aryl amines with benzylic substituents (i.e., α-branched aryl amines, e.g., 1, Scheme 1) are widely used building blocks for the synthesis of pharmaceuticals, agrochemicals, pesticides, chiral auxiliaries, and chiral ligands. New methods are needed for the preparation of α-branched aryl amines. Specifically, there is a need for methodology that prepares chiral α-branched aryl amines under mild and/or catalytic conditions. Amines with α-aryl substituents can be readily prepared from α-branched aryl phthalimides (cf., 2) by hydrazinolysis. The precursor α-branched aryl phthalimide functional group comprises many pharmaceuticals, agrochemicals, and pesticides.

Scheme 1: Depiction of generic α-branched aryl amine (1) and α-branced aryl phthalimide (2)

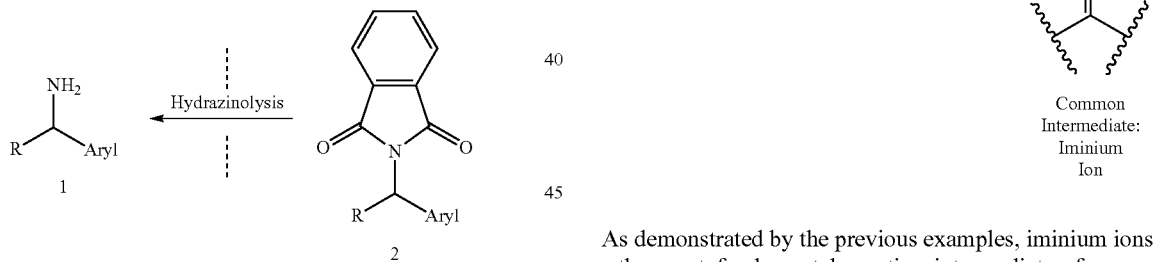

The Mannich and Ugi reactions are the oldest and most widely used methods for preparing complex amines (cf. Scheme 2, panels A and B). Under each of these conditions, an amine condenses with a ketone or aldehyde to form an imine or iminium ion (cf. 3) intermediate. Under the Mannich reaction conditions, this intermediate subsequently reacts with an enolizable ketone, aldehyde, or preformed enolate to give a β-amino carbonyl. Under the Ugi (multi-component) reaction conditions, an imine reacts with an isocyanide, and the resulting intermediate is subsequently trapped by, for example, water to give an α-amino amide. In the Petasis modification of the Mannich reaction, vinyl and aryl boronic acids are treated with a mixture of amine and carbonyl to give vinyl amines and aryl amines, respectively. A major practical advantage of these reactions includes the opportunity to exploit the multicomponent facets of these processes for the single-step preparation of complex amines.

Scheme 2: Representative reactions for the preparation of complex amines. a) General Mannic reaction, b) generic Ugi reaction, c) generic Petasis-modified Mannich reaction A) Mannich Reaction

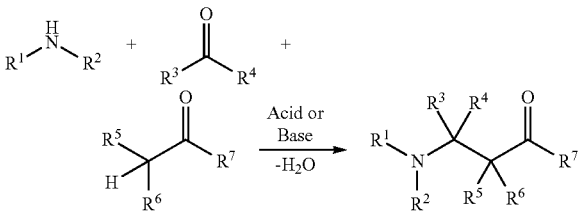

B) Ugi Reaction

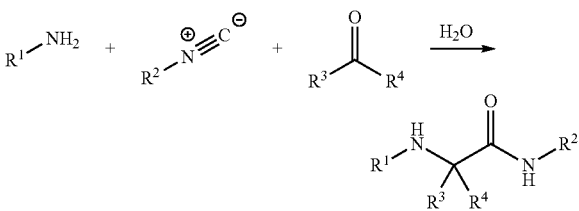

C) Petasis-Modified Mannic Reaction

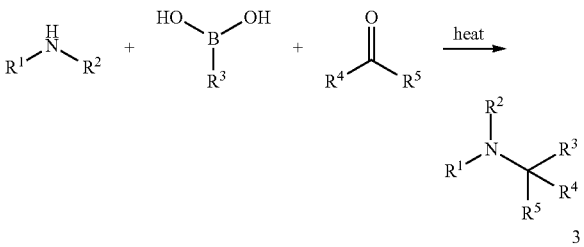

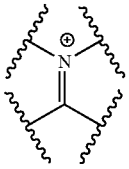

Common Intermediate: Iminium Ion

As demonstrated by the previous examples, iminium ions are the most fundamental reactive intermediates for processes that prepare amine-containing organic molecules. Iminium intermediates are highly electrophilic at carbon and are known to react with a myriad of nucleophiles to give products with complex and diverse structures. Methods have recently emerged for generating iminium ions from N,O-acetals (cf. 4, Scheme 3) in the presence of Lewis acids (for examples, see Renaud, P., Stojanovic, A. *Tetrahedron Letters* 1996, 37, 2569-2572, Stojanovic, A., Renaud, P., Schenk, K. *Helvetica Chimica Acta* 1998, 81, 268-284, Liu, R.-C., Huang, W., Ma, J.-Y., Wei, B.-G., Lin, G.-Q. *Tetrahedron Letters* 2009, 50, 4046-4049, Onomura, O., Ikeda, T., Kuriyama, M., Matsumura, Y., Kamogawa, S. *Heterocycles* 2010, 82, 325-332, Lee, W.-I., Jung, J.-W., Jang, J., Yun, H., Suh, Y.-G. *Tetrahedron Letters* 2013, 54, 5167-5171). Under these conditions, the Lewis acid reagent likely activates the N,O-acetal by coordinating to oxygen (cf. 5). Elimination of the Lewis acid-coordinated oxygen atom forms an iminium ion (cf. 6), which is poised to react intermolecularly with a nucleophile to form the amine product (cf. 7).

Scheme 3: Generic Lewis acid-mediated nucleophilic substitution reaction of an N,O-acetal.

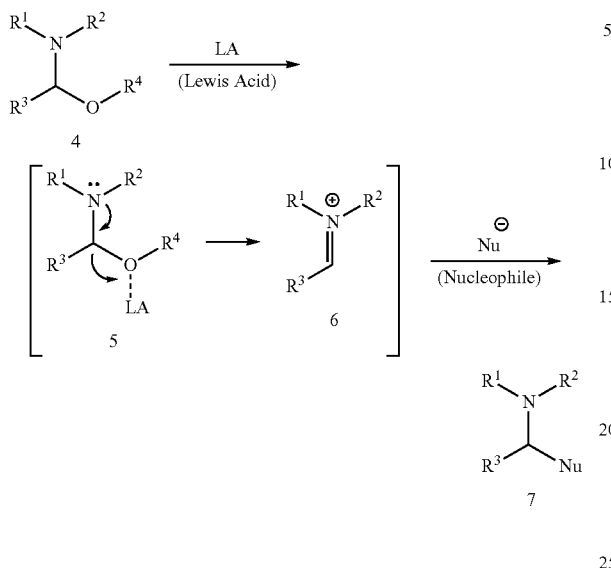

Despite the advances in the synthesis of complex nitrogen-containing organic molecules via the Mannich and Ugi reactions, alternative procedures that avoid the use of primary amines, boronic acids, and isocyanides would be beneficial when the desired molecules contain sensitive functional groups. In this regard, N,O-acetals are promising alternatives for the generation of iminium ion intermediates. Due to their potential utility, there is a need for improved methods for preparing N,O-acetals that are both more efficient and can give rise to a library of substrates. Additionally, the scope of nucleophiles that are capable of reacting with the putative iminium ion intermediates has not been fully explored.

SUMMARY

In one embodiment the invention provides methods for preparing N,O-acetals and methods for their conversion into α-branched aryl phthalimides and α-branched aryl amines. The compounds and methods of the invention are useful for preparing chiral aryl amines that are important building blocks for a variety of pharmaceutical and commercial compounds.

In one embodiment the invention provides a method for preparing an N,O-acetal of formula 4a:

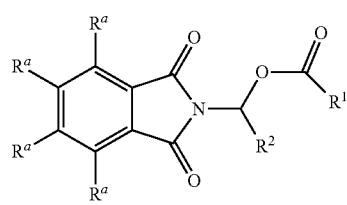

comprising:
(a) reacting a salt of formula 1a with an activated compound of formula 2a and an aldehyde of formula 3a,

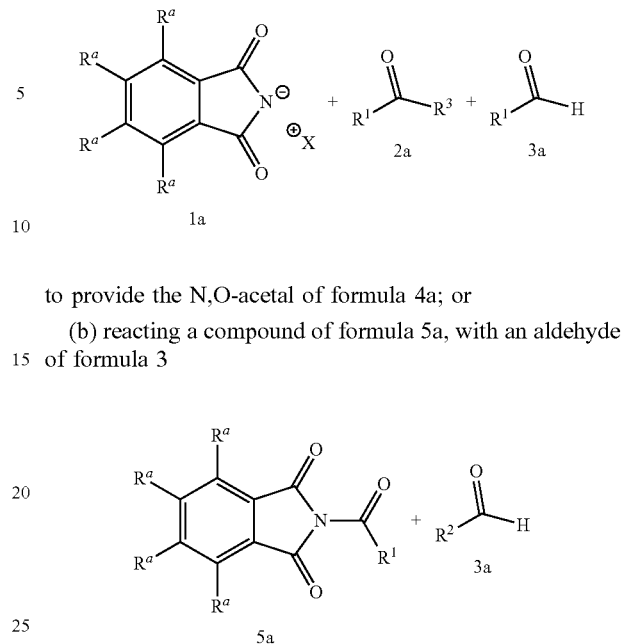

to provide the N,O-acetal of formula 4a; or
(b) reacting a compound of formula 5a, with an aldehyde of formula 3

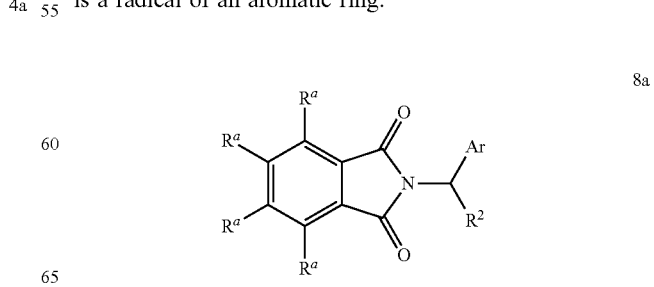

to provide the N,O-acetal of formula 4a;

wherein:

X is a suitable counter ion;

$R^1$ is $(C_1-C_{10})$alkyl, $(C_2-C_{10})$alkenyl or $(C_2-C_{10})$alkynyl wherein any $(C_1-C_{10})$alkyl, $(C_2-C_{10})$alkenyl, $(C_2-C_{10})$alkynyl is optionally independently substituted with one or more phenyl or halo;

$R^2$ is $(C_1-C_{10})$alkyl, $(C_2-C_{10})$alkenyl, $(C_2-C_{10})$alkynyl, aryl wherein any $(C_1-C_{10})$alkyl, $(C_2-C_{10})$alkenyl, $(C_2-C_{10})$alkynyl of $R^2$ is optionally substituted with one or more groups independently selected from halo, $(C_1-C_{10})$alkoxy and aryl and wherein any aryl of $R^2$ is optionally substituted with one or more groups independently selected from halo, $(C_1-C_8)$alkyl, $(C_1-C_8)$alkoxy, nitro, and aryl;

$R^3$ is chloro, fluoro, bromo, cyano, or $(C_1-C_6)$alkanoyl, that is optionally substituted with one or more halo; and each $R^a$ is independently selected from H, halo, $(C_1-C_6)$alkyl, $(C_2-C_6)$alkenyl, $(C_2-C_6)$alkynyl and $(C_1-C_6)$alkoxy wherein any $(C_1-C_6)$alkyl, $(C_2-C_6)$alkenyl, $(C_2-C_6)$alkynyl and $(C_1-C_6)$alkoxy is optionally independently substituted with one or more halo.

In one embodiment the invention provides a method for preparing an α-aryl phthalimide of formula 8a, wherein Ar is a radical of an aromatic ring:

comprising treating a corresponding compound of formula 7a:

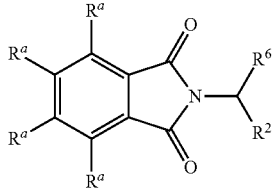

with an aromatic ring Ar and a suitable reagent in a suitable solvent to provide the α-aryl phthalimide 8a, wherein:

$R^2$ is $(C_1-C_{10})$alkyl, $(C_2-C_{10})$alkenyl, $(C_2-C_{10})$alkynyl, aryl wherein any $(C_1-C_{10})$alkyl, $(C_2-C_{10})$alkenyl, $(C_2-C_{10})$ alkynyl of $R^2$ is optionally substituted with one or more groups independently selected from halo, $(C_1-C_{10})$alkoxy and aryl and wherein any aryl of $R^2$ is optionally substituted with one or more groups independently selected from halo, $(C_1-C_8)$alkyl, $(C_1-C_8)$alkoxy, nitro, and aryl;

$R^6$ is a —OC(=O)$R^1$ or halo;

Ar is a hydrocarbon aromatic ring that is optionally substituted with one or more groups independently selected from halo, nitro, $(C_1-C_6)$alkyl, $(C_2-C_6)$alkenyl, $(C_2-C_6)$alkynyl, $(C_1-C_6)$alkoxy and $(C_2-C_6)$alkanoyloxy, wherein any $(C_1-C_6)$alkyl, $(C_2-C_6)$alkenyl, $(C_2-C_6)$alkynyl, $(C_1-C_6)$alkoxy and $(C_2-C_6)$alkanoyloxy is optionally substituted with one or more halo; and each $R^a$ is independently selected from H, halo, $(C_1-C_6)$alkyl, $(C_2-C_6)$alkenyl, $(C_2-C_6)$alkynyl and $(C_1-C_6)$alkoxy wherein any $(C_1-C_6)$alkyl, $(C_2-C_6)$alkenyl, $(C_2-C_6)$alkynyl and $(C_1-C_6)$alkoxy is optionally independently substituted with one or more halo.

In one embodiment the invention provides a method for preparing a compound of formula 10a,

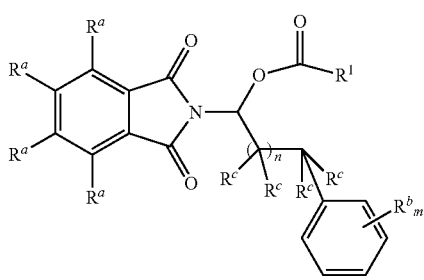

comprising treating a corresponding compound of formula 4a:

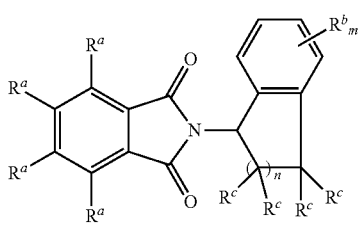

with a suitable reagent in a suitable solvent to provide the compound of formula 10a;

wherein:

$R^1$ is $(C_1-C_{10})$alkyl, $(C_2-C_{10})$alkenyl or $(C_2-C_{10})$alkynyl wherein any $(C_1-C_{10})$alkyl, $(C_2-C_{10})$alkenyl, $(C_2-C_{10})$alkynyl is optionally independently substituted with one or more phenyl or halo;

each $R^a$ is independently selected from H, halo, $(C_1-C_6)$ alkyl, $(C_2-C_6)$alkenyl, $(C_2-C_6)$alkynyl and $(C_1-C_6)$alkoxy wherein any $(C_1-C_6)$alkyl, $(C_2-C_6)$alkenyl, $(C_2-C_6)$alkynyl and $(C_1-C_6)$alkoxy is optionally independently substituted with one or more halo;

each $R^b$ is independently selected from halo, $(C_1-C_6)$alkyl and $(C_1-C_6)$alkoxy;

m is 0, 1, 2, 3 or 4;

each $R^c$ is independently selected from H or methyl; and n is 1, 2 or 3.

In one embodiment the invention also provide a method comprising performing an intramolecular cyclization by subjecting a compound of formula 4b:

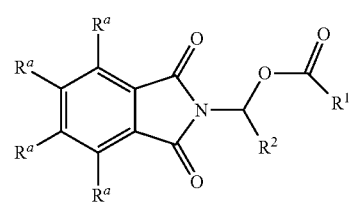

wherein $R^2$ comprises a group that can cyclize intramolecularly by displacing the group —O(C=O)$R^1$ to conditions suitable to produce the intramolecular cyclization.

In one embodiment the invention also provides the synthetic processes and the compounds described in the Examples herein.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that the values and embodiments described herein are values or embodiments for all formulas described herein (e.g., formulas 1a-11a). It is to be understood that two or more values or embodiments may be combined.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo $(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy $(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, naphthyl or anthacenyl or a phenyl fused to a saturated of partially unsaturated carbocyclic ring or 3 to 8 carbons; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for X is sodium or potassium.

A specific group or compounds include compounds wherein each $R^a$ is H.

A specific value for $R^1$ is $(C_1-C_{10})$alkyl.

In one embodiment the compound of formula 1a is treated with the compound 2a in a suitable solvent in the presence of a suitable organic base. In one embodiment the base is an amine base. In one embodiment the amine base is a tertiary amine base. In one embodiment the base is triethylamine, diisopropylethylamine, or pyridine.

In one embodiment the compound of formula 1a is treated with the compound 2a and aldehyde 3a in the presence of a suitable Lewis acid. In one embodiment the Lewis acid comprises titanium tetrachloride, boron trifluoride, trimethylsilyl trifluoromethanesulfonate, lithium tetrafluoroborate, or silver trifluoromethanesulfonate in the presence of chlorotrimethylsilane. In one embodiment the Lewis acid is lithium tetrafluoroborate or lithium chloride.

In one embodiment the compound of formula 1a is treated with the compound 2a and aldehyde 3a in the presence of dichloromethane, chloroform, tetrahydrofuran, toluene, benzene, hexanes, pentane, or diethyl ether. In one embodiment the compound of formula 1a is treated with the compound 2a and aldehyde 3a in the presence of acetonitrile, acetone, dichloromethane, chloroform, or ethyl acetate. In one embodiment the compound of formula 1a is treated with the compound 2a and aldehyde 3a in the presence of acetonitrile, acetone, dichloromethane, chloroform, toluene, or ethyl acetate.

In one embodiment the compound 2a is added to a mixture of phthalimide potassium salt 1a, and aldehyde 3a, $LiBF_4$, and triethylamine in acetonitrile to provide N-phthalimido-O-acyl-N,O-acetal 4a.

One embodiment provides further conversion of a compound of formula 4a to a corresponding compound of formula 6a.

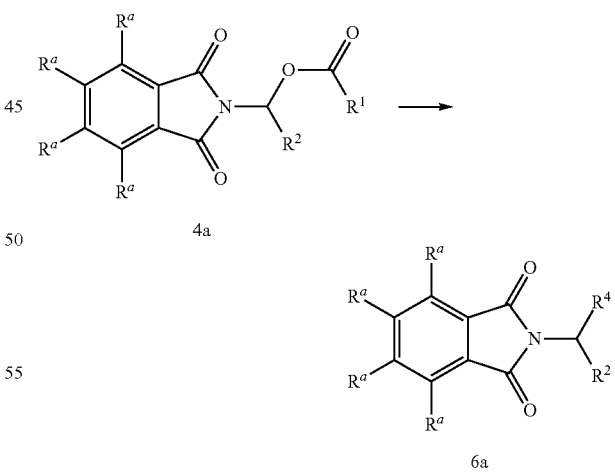

wherein:

$R^1$ is $(C_1-C_{10})$alkyl, $(C_2-C_{10})$alkenyl or $(C_2-C_{10})$alkynyl wherein any $(C_1-C_{10})$alkyl, $(C_2-C_{10})$alkenyl, $(C_2-C_{10})$alkynyl is optionally independently substituted with one or more phenyl or halo;

$R^2$ is $(C_1-C_{10})$alkyl, $(C_2-C_{10})$alkenyl, $(C_2-C_{10})$alkynyl, aryl wherein any $(C_1-C_{10})$alkyl, $(C_2-C_{10})$alkenyl, $(C_2-C_{10})$ alkynyl of $R^2$ is optionally substituted with one or more groups independently selected from halo, $(C_1-C_{10})$alkoxy and aryl and wherein any aryl of $R^2$ is optionally substituted with one or more groups independently selected from halo, $(C_1-C_8)$alkyl, $(C_1-C_8)$alkoxy, nitro, and aryl; and $R^4$ is a halo; and each $R^a$ is independently selected from H, halo, $(C_1-C_6)$alkyl, $(C_2-C_6)$alkenyl, $(C_2-C_6)$alkynyl and $(C_1-C_6)$alkoxy wherein any $(C_1-C_6)$alkyl, $(C_2-C_6)$alkenyl, $(C_2-C_6)$alkynyl and $(C_1-C_6)$alkoxy is optionally independently substituted with one or more halo.

In one embodiment the invention provides a method for preparing an α-aryl phthalimide of formula 8a, wherein Ar is a radical of an aromatic ring:

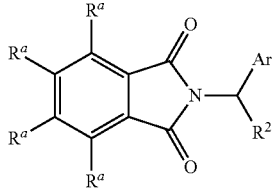

8a comprising treating a corresponding compound of formula 7a:

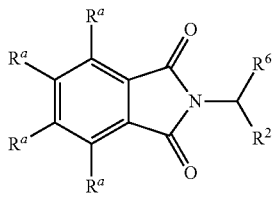

7a with an aromatic ring Ar and a suitable reagent in a suitable solvent to provide the α-aryl phthalimide 8a. In one embodiment the suitable solvent comprises is an aprotic solvent. In one embodiment the aprotic solvent comprises dichloromethane, chloroform, tetrahydrofuran, toluene, benzene, hexanes, pentane, or diethyl ether. In one embodiment the suitable solvent comprises a halogenated solvent. In one embodiment the halogenated solvent comprises, dichloromethane, chloroform, or carbon tetrachloride. In one embodiment the solvent is dichloromethane. In one embodiment the treating is carried out in the presence of a chiral complexing agent. In one embodiment a chiral complexing agent is used to provide an enantiomerically enriched α-aryl phthalimide 8a. In one embodiment the chiral complexing agent is used to provide a stereochemically enriched α-aryl phthalimide 8a wherein the stereochemistry of the carbon atom joining the Ar group and the $R^2$ of group of compound 8a is enriched in either the R stereochemistry or the S stereochemistry. In one embodiment the chiral complexing agent is a chiral phase transfer catalyst. In one embodiment the chiral phase transfer catalyst comprises a chiral phosphoric acid conjugate base, or a chiral borate.

One embodiment provides further conversion of α-aryl phthalimide 8a to aryl amine 9a comprising treating the α-aryl phthalimide 8a under suitable conditions to provide the corresponding α-branched aryl amine 9a:

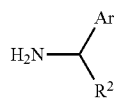

9a or a salt thereof.

One embodiment provides further conversion compound 10a to compound 11a comprising treating the compound of formula 10a under suitable conditions to provide the corresponding compound of formula 11a:

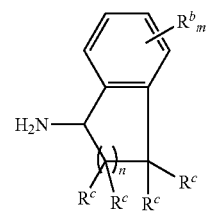

11a or a salt thereof.

It was found that treating a solution (e.g. dichloromethane) of N-phthalimido-O-acyl-N,O-acetal 8 (Scheme 4) and anisole with boron trifluoride diethyl etherate gives rise to α-aryl phthalimide 10. This approach is thought to proceed through N-phthaloyl iminium ion 9, which is subsequently trapped by anisole via electrophilic aromatic substitution. Alternative Lewis acids that could also mediate the reaction include titanium tetrachloride, trimethylsilyl trifluoromethanesulfonate, and a combination of chlorotrimethylsilane and silver(I) trifluoromethanesulfonate. Treating α-aryl phthalimide 10 with hydrazine hydrate cleaved the phthalimide group to give rise to α-branched aryl amine 11.

Scheme 4: Initial example for the preparation of α-branched aryl phthalimides (cf. 10) and α-branched aryl amines (cf. 11).

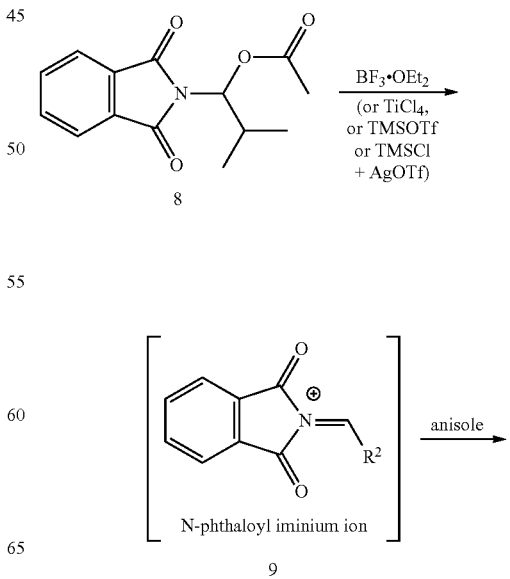

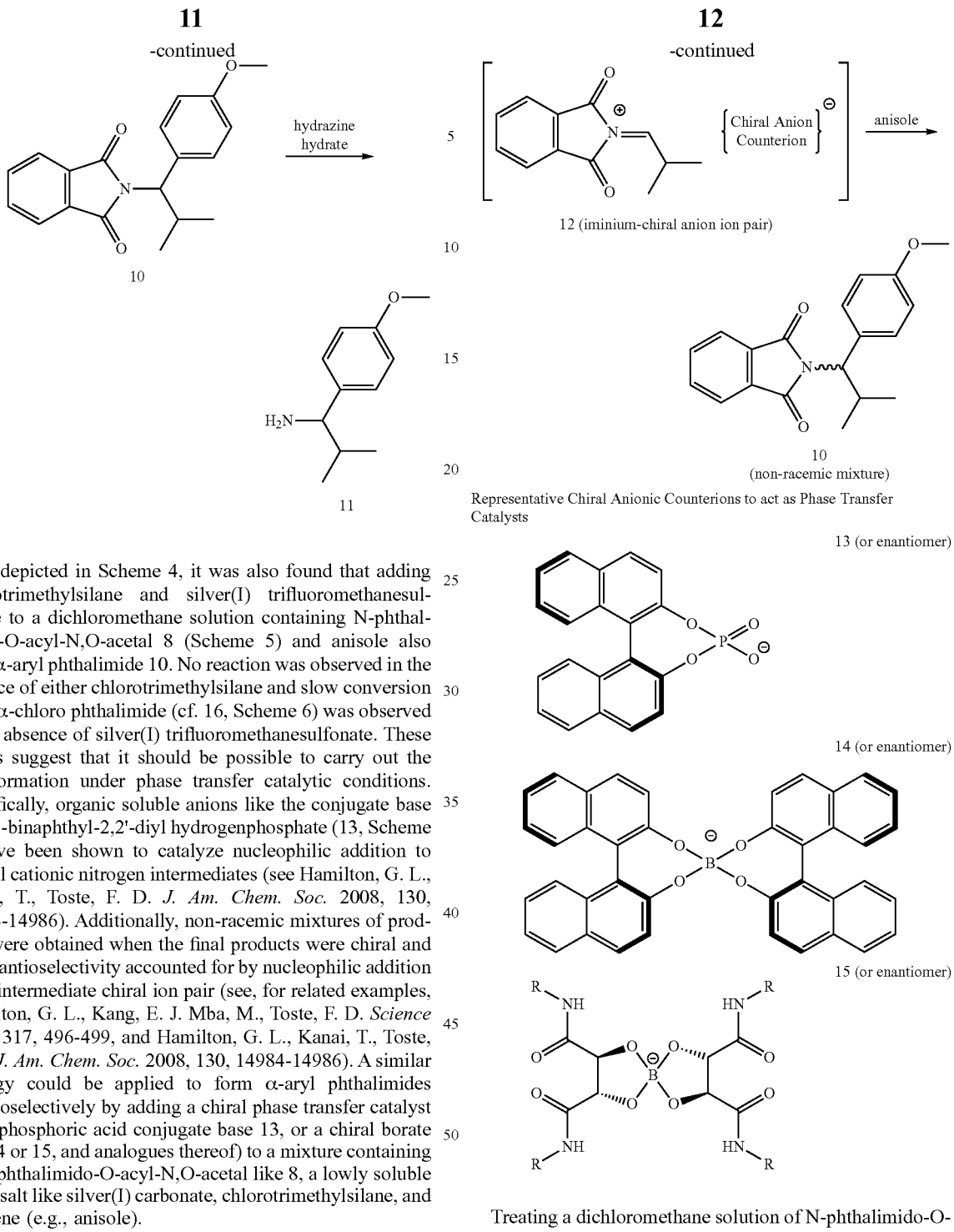

As depicted in Scheme 4, it was also found that adding chlorotrimethylsilane and silver(I) trifluoromethanesulfonate to a dichloromethane solution containing N-phthalimido-O-acyl-N,O-acetal 8 (Scheme 5) and anisole also gave α-aryl phthalimide 10. No reaction was observed in the absence of either chlorotrimethylsilane and slow conversion to an α-chloro phthalimide (cf. 16, Scheme 6) was observed in the absence of silver(I) trifluoromethanesulfonate. These results suggest that it should be possible to carry out the transformation under phase transfer catalytic conditions. Specifically, organic soluble anions like the conjugate base of 1,1'-binaphthyl-2,2'-diyl hydrogenphosphate (13, Scheme 5) have been shown to catalyze nucleophilic addition to achiral cationic nitrogen intermediates (see Hamilton, G. L., Kanai, T., Toste, F. D. *J. Am. Chem. Soc.* 2008, 130, 14984-14986). Additionally, non-racemic mixtures of products were obtained when the final products were chiral and the enantioselectivity accounted for by nucleophilic addition to an intermediate chiral ion pair (see, for related examples, Hamilton, G. L., Kang, E. J. Mba, M., Toste, F. D. *Science* 2007, 317, 496-499, and Hamilton, G. L., Kanai, T., Toste, F. D. *J. Am. Chem. Soc.* 2008, 130, 14984-14986). A similar strategy could be applied to form α-aryl phthalimides enantioselectively by adding a chiral phase transfer catalyst (e.g., phosphoric acid conjugate base 13, or a chiral borate like 14 or 15, and analogues thereof) to a mixture containing an N-phthalimido-O-acyl-N,O-acetal like 8, a lowly soluble silver salt like silver(I) carbonate, chlorotrimethylsilane, and an arene (e.g., anisole).

Scheme 5: Proposed catalytic enantioselective arylation of N-phthalimido-O-acyl-N,O-acetals via asymmetric phase transfer catalysis conditions.

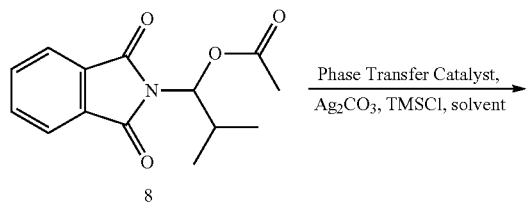

Treating a dichloromethane solution of N-phthalimido-O-acyl-N,O-acetal 8 with aluminum trichloride gave α-chloro phthalimide 16 (Scheme 6). Adding boron trifluoride etherate to a dichloromethane solution of N-phthalimido-O-acyl-N,O-acetal 8 and magnesium bromide diethyl etherate gave α-bromo phthalimide 17. Adding boron trifluoride diethyl etherate to a dichloromethane solution of N-phthalimido-O-acyl-N,O-acetal 8 and tetrabutylammonium iodide gave α-iodo phthalimide 18. Each of these α-halo phthalimides is converted into the corresponding α-branched aryl phthalimide when treated with an arene and a silver salt like silver(I) iodide or silver(I) trifluoromethanesulfonate. This suggests that each of the α-halo phthalimides should be amenable to the asymmetric phase transfer catalysis protocol discussed previously and depicted in Scheme 5. Additionally, ureas, thioureas, and other related reagents with a high affinity for halogen atoms should be capable of generating α-branched aryl phthalimides from α-halo phthalimides by halogen atom abstraction and subsequent electrophilic aromatic substitution with a chiral ion pair like 12 (see, for related examples, Raheem, I. T., Thiara, P. S., Peterson, E. A., Jacobsen, E. N. *J. Am. Chem. Soc.* 2007, 129, 13404-13405).

Scheme 6: Examples demonstrating the preparation of α-halo phthalimides and an alternative chiral ion pair to be used for the enantioselective preparation of α-branched aryl phthalimides.

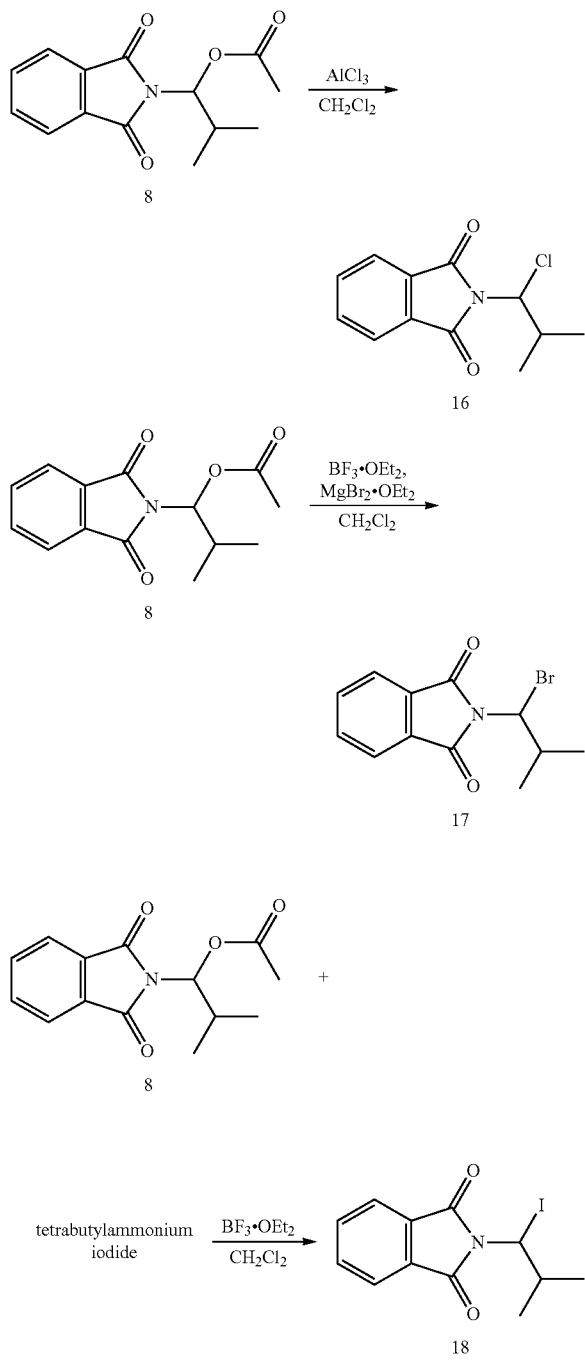

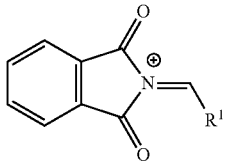

(Iminium-urea-halide chiral ion pair)

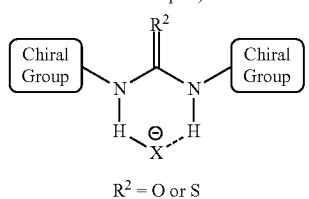

$R^2$ = O or S

Treating N-phthalimido-O-acyl-N,O-acetal 8 with a sub-stoichiometric amount (i.e., 0.3 equiv) of trimethylsilyl trifluoromethanesulfonate (TMSOTf) or trifluoromethanesulfonic acid (TfOH) in the presence of anisole (5 equiv) and with toluene as solvent cleanly produced α-aryl phthalimide 10. A proposed catalytic cycle for the acid-catalyzed arylation of N-phthalimido-O-acyl-N,O-acetals involves a pathway similar to a prototypical electrophilic aromatic substitution reaction. The catalytic cycle is initiated by protonating an ester oxygen with the strong acid, TfOH. The resulting oxonium eliminates acetic acid to generate N-phthaloyl iminium ion 9, which reacts via electrophilic aromatic substitution with anisole. Proton transfer from a strongly acidic arenium ion simultaneously forms α-aryl phthalimide 10 and achieves turnover of the acid catalyst. A related catalytic cycle could be proposed to account for the catalytic activity of TMSOTf that involves a silylated oxoinium intermediate. However, hydrolysis of TMSOTf by trace water to form TfOH in situ cannot be ruled out, in which case, the TfOH acid-catalyzed pathway would likely be responsible for generating product.

These results suggest that it should be possible to prepare non-racemic mixtures of α-aryl phthalimides if a chiral Brønsted acid catalyst was used. Similar to the methodology presented in Schemes 5 and 6, the conjugate base of a chiral Brønsted acid could act as chiral complexing reagent. Under the acid-catalyzed pathway discussed above, the resulting N-phthaloyl iminium ion would complex with the chiral conjugate base to form a chiral ion pair. The chiral ion pair could be a source enantioinduction in the subsequent electrophilic aromatic substitution reaction. A representative series of chiral Brønsted acids include chiral phosphoric acids, chiral phosphoramides, chiral sulfonimides, chiral sulfonic acids, and chiral carboxylic acids (for examples of use these types of chiral Brønsted acids in asymmetric catalysis see Parmar, D.; Sugiono, E.; Raja, S.; Rueping, M. *Chem. Rev.* 2014, 114, 9047-9153). Additionally, a chiral urea or thiourea could facilitate an enantioselective reaction by complexing to the conjugate base of an achiral Brønsted acid via hydrogen bonding (for example, see Xu, H.; Zuend, S. J.; Woll, M. G.; Tao, Y.; Jacobsen, E. N. *Science* 2010, 327, 986-990). By hydrogen bonding to the an achiral conjugate base like a sulfonate anion, the urea or thiourea forms a chiral anion, which would give rise to a chiral ion pair in the presence of a cation like N-phthaloyl iminium ion 9.

Heating a mixture of anisole and α-iodo phthalimide 18 gave rise to α-branched aryl phthalimide 10. The absence of additional reagents is attractive for preparing α-branched aryl phthalimides from benzenoids that have sensitive functional groups that are not compatible with strong Lewis acids.

Scheme 7: Representative example for the preparation of α-branched aryl phthalimides via thermal generation of N-phthaloyl iminium ions from α-iodo phthalimides.

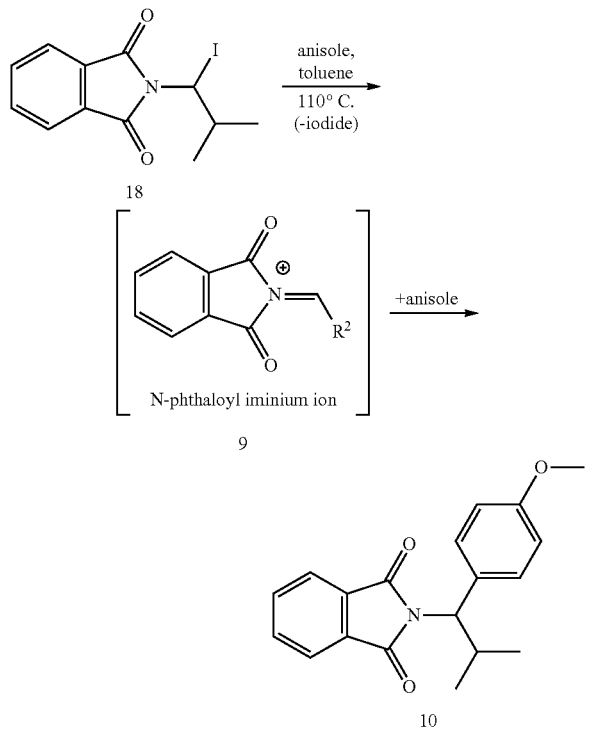

One embodiment of the invention includes the synthesis of the N-phthalimido-O-acyl-N,O-acetals necessary for preparing the α-branched aryl phthalimides and α-branched aryl amines. While studying the aldol reaction of lithium-coordinated imides, it was found that a mixture of N-acylphthalimide 20, isobutyraldehyde (21), LiBF$_4$, and triethylamine in acetonitrile gives rise to N-phthalimido-O-acyl-N,O-acetal 22. The process occurs at room temperature and greater than 99% conversion is observed within sixty minutes of reaction time. The reaction represents a net "insertion" of the aldehyde π-bond into the C—N σ-bond. After a series of control experiments, it was shown that this surprising outcome does not occur without addition of a metal Lewis acid (e.g., LiBF$_4$) and tertiary amine (e.g., triethylamine).

Scheme 8: Representative example for the preparation of N-phthalimido-O-acyl-N,O-acetals (22) from acyl phthalimides (cf. 20) and aldehydes.

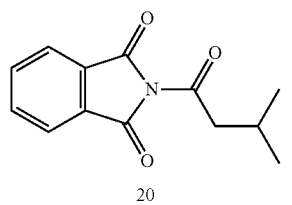

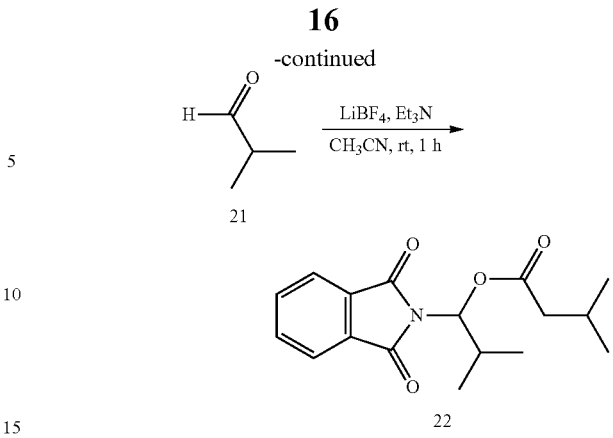

Molecules with the N-phthalimido-O-acyl-N,O-acetal functional group have been rarely observed, however, one such report includes the use of a stoichiometric amount of lead(IV) acetate to convert threonine-derived α-phthalimido acid (cf. 23, Scheme 9) into the corresponding N-phthalimido-O-acetyl-N,O-acetal, 24 (see Renaud, P., Stojanovic, A. *Tetrahedron Letters* 1996, 37, 2569-2572). In a follow-up report, the valine-derived analogue 26 was prepared by a similar procedure (see Stojanovic, A., Renaud, P., Schenk, K. *Helvetica Chimica Acta* 1998, 81, 268-284). To both act as a second specific example and ensure proper assignment to the molecules contained within this application, 26 was prepared by treating a mixture of N-acylphthalimide 25 and isobutyraldehyde (21) dissolved in acetonitrile with LiBF$_4$ and triethylamine. After purification, N-phthalimido-O-acyl-N,O-acetal 26 was obtained, and the purified material had characterization data that was in strong agreement the with the previously reported spectral data.

Scheme 9: Example of a previous approach to the preparation of N-phthalimido-O-acyl-N,O-acetals and application of the current protocol to synthesis of known compound 26.

Previous Approach

Current Approach

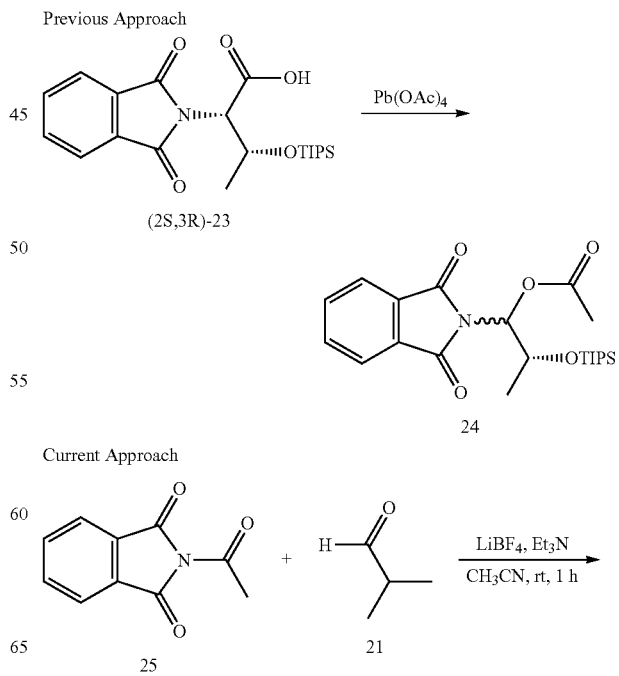

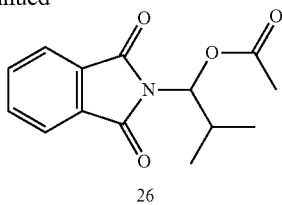

26

Having discovered an approach for the synthesis of N-phthalimido-O-acyl-N,O-acetals, the protocol was optimized to improve the practicality and make the process more operationally simple. The N-acylphthalimide starting materials are routinely prepared by treating a dichloromethane suspension of phthalimide potassium salt (27) and diisopropylethylamine (DIPEA) with an acyl chloride (e.g., 28). Because the presence of isobutyraldehyde and LiBF$_4$ will not be detrimental to the formation of the N-acyl phthalimide, a one-pot procedure was developed in which the N-acylphthalimide was generated in situ and converted into the corresponding N-phthalimido-O-acyl-N,O-acetal product. Specifically, addition of acetyl chloride (28) to a mixture of phthalimide potassium salt (27), isobutyraldehyde (21), LiBF$_4$, and diisopropylethylamine in acetonitrile gave rise to N-phthalimido-O-acyl-N,O-acetal 26.

Scheme 10: Synthesis of N-acyl phthalimide 25 and the one-pot synthesis of N-phthalimido-O-acyl-N,O-acetal 26.

Synthesis of N-Acyl Phthalimides

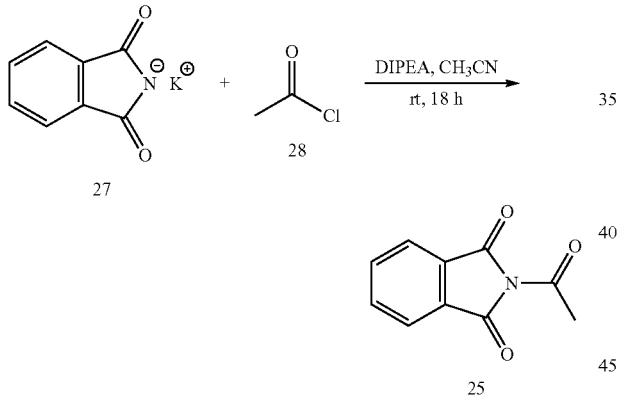

One-Pot Synthesis of N-Phthalimido-O-acyl-N,O-acetals

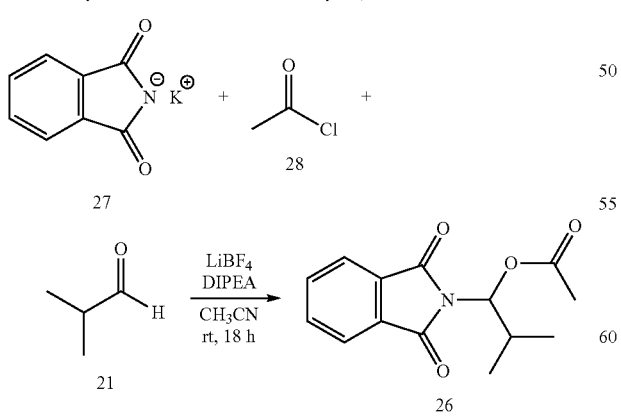

Schemes 11-13

Schemes 11-13 illustrate how the methods and synthetic intermediates of the invention can be used to prepare certain specific pharmaceutical agents. It will be understood that the methods illustrated in Schemes 11-13 are not limiting and that the methods and intermediates of the invention are generally useful for preparing a wide range of α-branched aryl amines that have utility in a range of chemical applications.

The methods of the invention can be applied to the preparation α-branched aryl amines that are key intermediates in the synthesis of molecules currently marketed as active pharmaceutical ingredients. Citrizine dihydrochloride is a histamine H1-receptor antagonist and is marketed as an antihistamine and for alleviating cold and allergy symptoms. Scheme 11 depicts an approach for the preparation of diaryl amine 33, which is a key intermediate in the synthesis of citrizine dihydrochloride (see Pflum, D. A., Krishnamurthy, D., Han, Z., Wald, S. A., Senanayake, C. H. *Tetrahedron Letters* 2002, 43, 923-926). Application of enantioselective arylation conditions would provide a non-racemic sample of citrizine dihydrochloride.

Scheme 11: Proposed synthesis of citrizine dihydrochloride using the invented methodology.

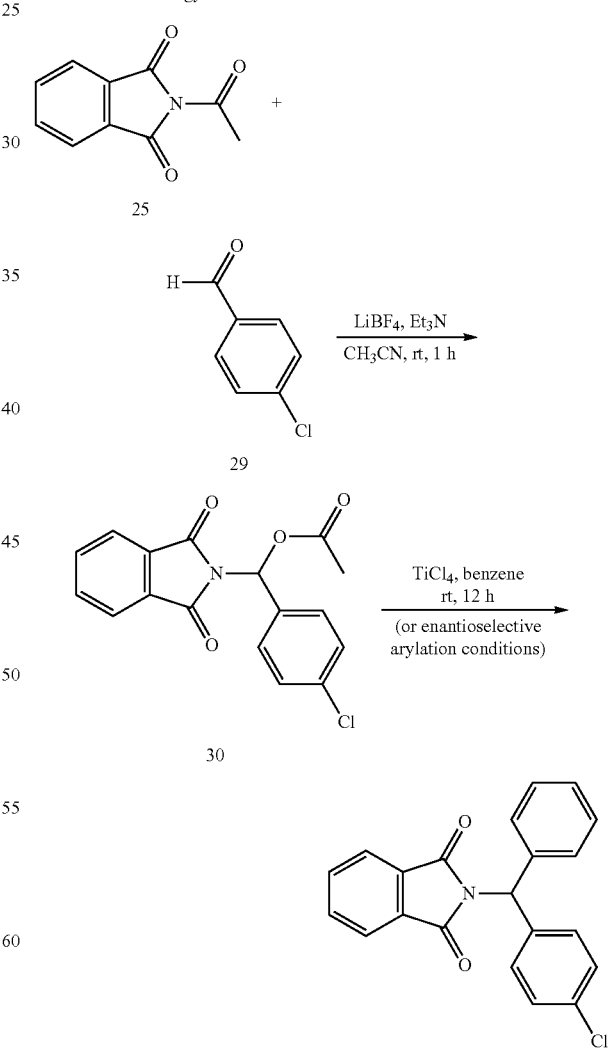

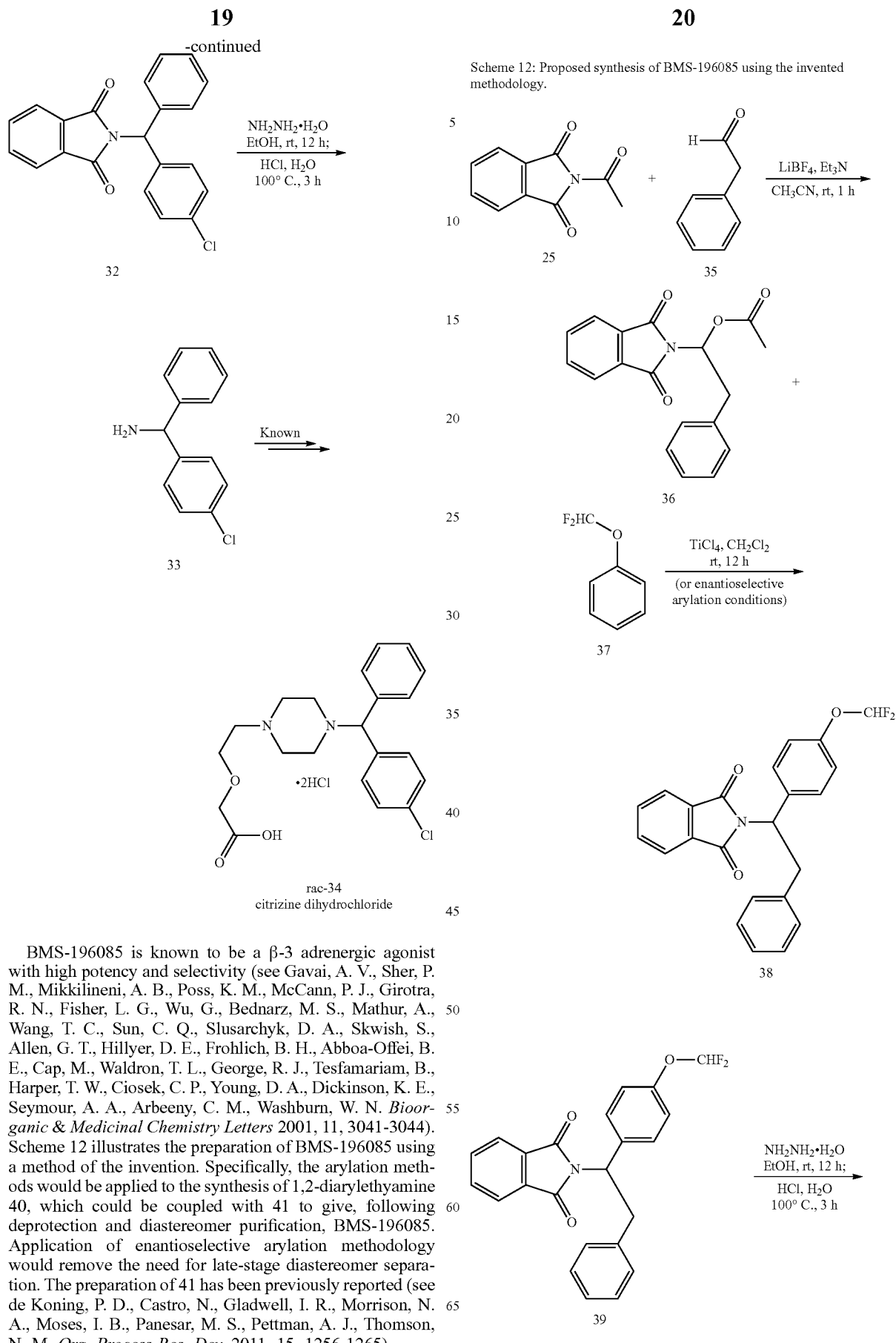

Scheme 12: Proposed synthesis of BMS-196085 using the invented methodology.

BMS-196085 is known to be a β-3 adrenergic agonist with high potency and selectivity (see Gavai, A. V., Sher, P. M., Mikkilineni, A. B., Poss, K. M., McCann, P. J., Girotra, R. N., Fisher, L. G., Wu, G., Bednarz, M. S., Mathur, A., Wang, T. C., Sun, C. Q., Slusarchyk, D. A., Skwish, S., Allen, G. T., Hillyer, D. E., Frohlich, B. H., Abboa-Offei, B. E., Cap, M., Waldron, T. L., George, R. J., Tesfamariam, B., Harper, T. W., Ciosek, C. P., Young, D. A., Dickinson, K. E., Seymour, A. A., Arbeeny, C. M., Washburn, W. N. *Bioorganic & Medicinal Chemistry Letters* 2001, 11, 3041-3044). Scheme 12 illustrates the preparation of BMS-196085 using a method of the invention. Specifically, the arylation methods would be applied to the synthesis of 1,2-diarylethyamine 40, which could be coupled with 41 to give, following deprotection and diastereomer purification, BMS-196085. Application of enantioselective arylation methodology would remove the need for late-stage diastereomer separation. The preparation of 41 has been previously reported (see de Koning, P. D., Castro, N., Gladwell, I. R., Morrison, N. A., Moses, I. B., Panesar, M. S., Pettman, A. J., Thomson, N. M. *Org. Process Res. Dev.* 2011, 15, 1256-1265).

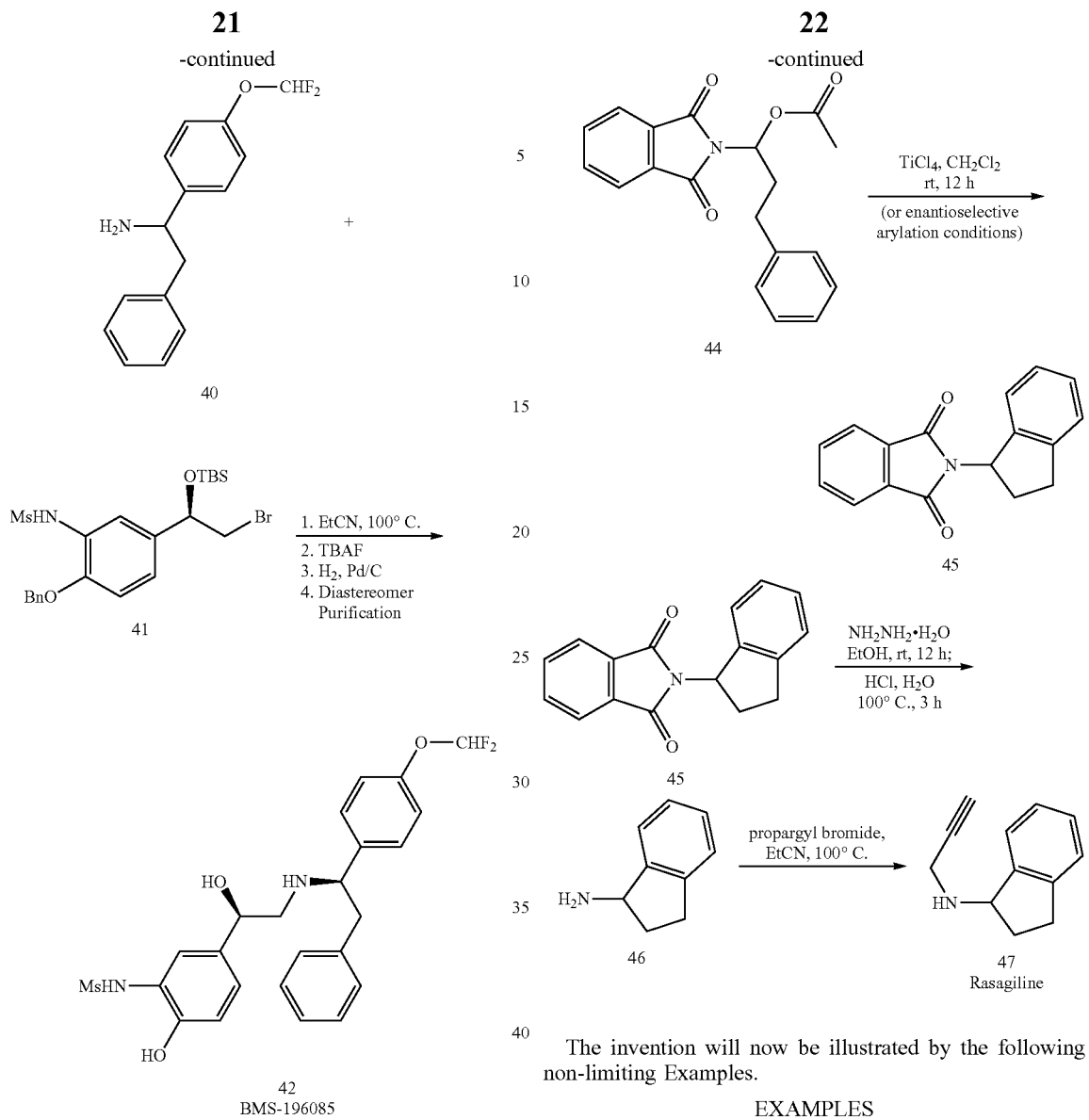

Rasagiline (47) is a monoamine oxidase inhibitor that is prescribed to patients with early onset Parkinson's disease. Scheme 13 depicts an application of the proposed methodology for the preparation of rasagiline. Use of enantioselective arylation conditions will produce a non-racemic sample rasagiline.

Scheme 13: Proposed synthesis of rasagiline using the invented methodology.

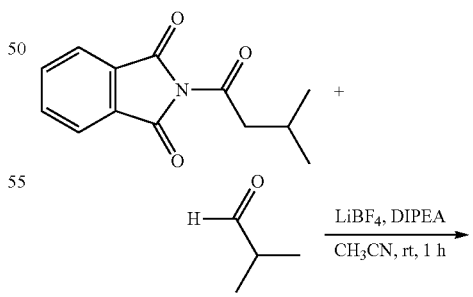

The invention will now be illustrated by the following non-limiting Examples.

EXAMPLES

Example 1

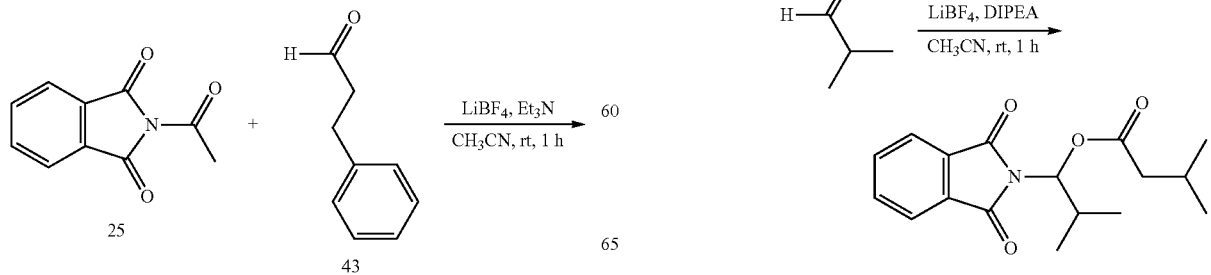

Spectral Data for the Product of Example 1: $^1$H NMR (300 MHz, CDCl$_3$): δ 7.88 (dd, J=3.1, 5.5 Hz, 2H), 7.75 (dd, J=3.1, 5.5 Hz, 2H), 6.20 (d, J=10.4 Hz, 1H), 2.80-2.99 (m, 1H), 2.23 (br d, J=6.5 Hz, 2H), 2.10 (m, 1H), 1.08 (d, J=6.6 Hz, 3H), 0.912 (d, J=6.6 Hz, 3H), 0.907 (d, J=6.6 Hz, 3H), and 0.89 (d, J=6.7 Hz, 3H). HR ESI-MS: [C$_{17}$H$_{21}$NO$_4$+Na]$^+$ requires 326.1363. Found 326.1364.

Example 2

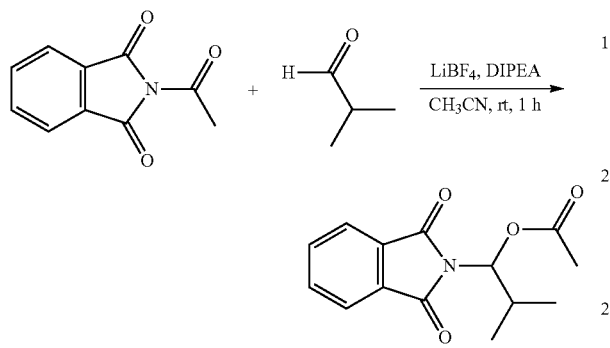

Spectral Data for the Product of Example 2: $^1$H NMR (300 MHz, CDCl$_3$): δ 7.89 (dd, J=3.1, 5.7 Hz, 2H), 7.76 (dd, J=3.2, 5.5 Hz, 2H), 6.23 (d, J=10.4 Hz, 1H), 2.90 (d septet, J=10.4, 6.8, 1H), 2.10 (s, 3H), 1.09 (d, J=6.7 Hz, 3H), and 0.89 (d, J=6.8 Hz, 3H). HR ESI-MS: [C$_{14}$H$_{15}$NO$_4$+Na]$^+$ requires 284.0893. Found 284.0892.

Example 3

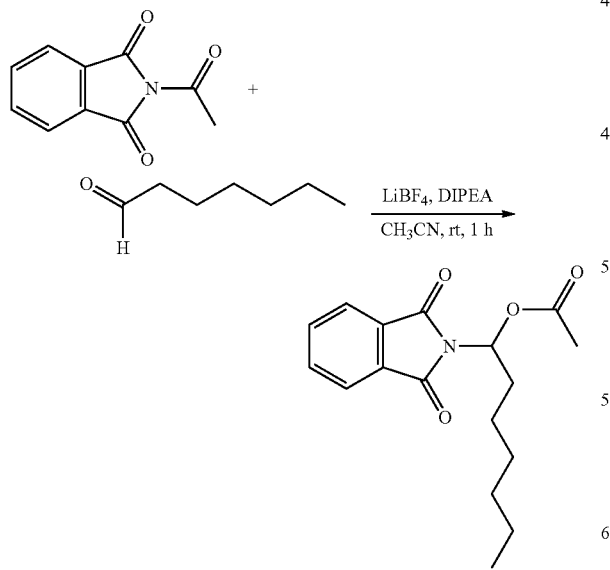

Spectral Data for the Product of Example 3: $^1$H NMR (300 MHz, CDCl$_3$): δ 7.88 (dd, J=3.1, 5.6 Hz, 2H), 7.76 (dd, J=3.1, 5.4 Hz, 2H), 6.60 (dd, J=6.9, 8.0 Hz, 1H), 2.13-2.37 (m, 2H), 2.08 (s, 3H), 1.21-1.44 (m, 3H), and 0.82-0.94 (m).

Example 4

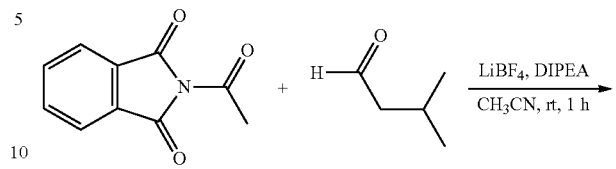

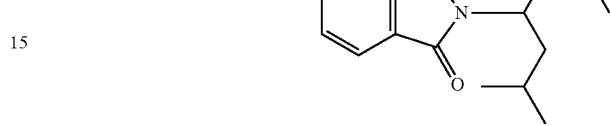

Spectral Data for the Product of Example 4: $^1$H NMR (300 MHz, CDCl$_3$): δ 7.88 (dd, J=3.1, 5.4 Hz, 2H), 7.75 (dd, J=3.1, 5.6 Hz, 2H), 6.70 (dd, J=6.8, 8.2 Hz, 1H), 2.17-2.33 (m, 1H), 1.97-2.14 (m, 1H), 2.07 (s, 3H), 1.49-1.69 (m, 1H), 0.98 (d, J=6.6 Hz, 3H), and 0.96 (d, J=6.6 Hz, 3H).

Example 5

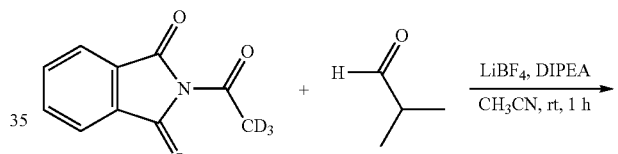

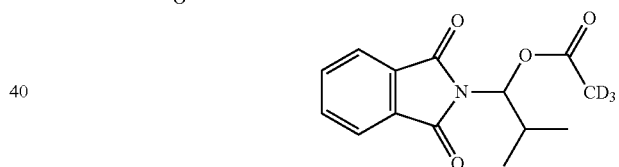

Spectral Data for the Product of Example 5: $^1$H NMR (300 MHz, CDCl$_3$): δ 7.88 (dd, J=3.1, 5.7 Hz, 2H), 7.76 (dd, J=3.2, 5.5 Hz, 2H), 6.23 (d, J=10.4 Hz, 1H), 2.90 (d septet, J=10.4, 6.8 Hz, 1H), 1.08 (d, J=6.7 Hz, 3H), and 0.89 (d, J=6.8 Hz, 3H).

Example 6

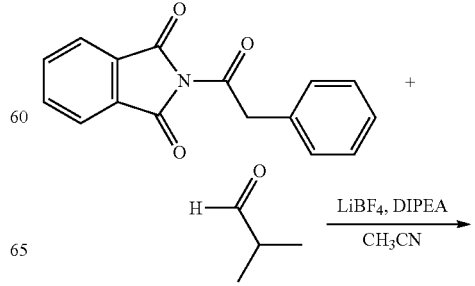

-continued

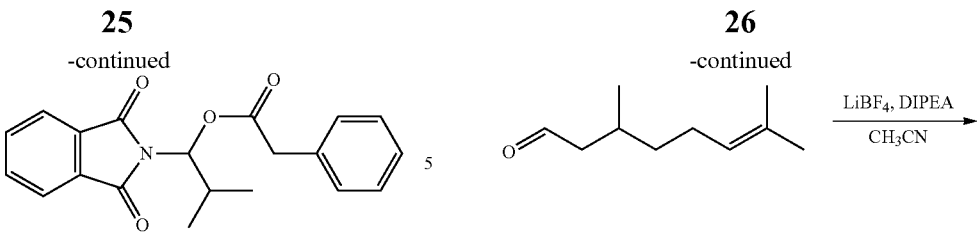

Spectral Data for the Product of Example 6: $^1$H NMR (300 MHz, CDCl$_3$): δ 7.86 (dd, J=3.1, 5.7 Hz, 2H), 7.74 (dd, J=3.2, 5.5 Hz, 2H), 7.13-7.36 (m, 5H), 6.19 (d, J=10.5 Hz, 1H), 3.68 (d, J=15.2 Hz, 1H), 3.62 (d, J=15.3 Hz, 1H), 2.90 (d septet, J=10.4, 6.6 Hz, 1H), 1.00 (d, J=6.7 Hz, 3H), and 0.87 (d, J=6.8 Hz, 3H). HR ESI-MS: [C$_{20}$H$_{19}$NO$_4$+Na]$^+$ requires 360.1206. Found 360.1209.

Example 7

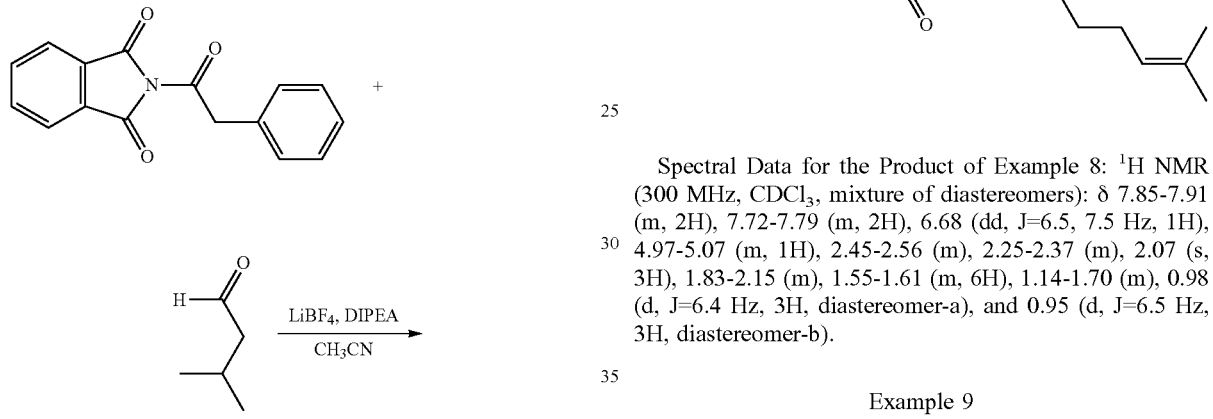

Spectral Data for the Product of Example 7: $^1$H NMR (300 MHz, CDCl$_3$): δ 7.86 (dd, J=3.1, 5.7 Hz, 2H), 7.74 (dd, J=3.2, 5.5 Hz, 2H), 6.72 (dd, J=6.8, 8.2 Hz, 1H), 6.68 (dd, J=6.8, 8.2 Hz, 1H), 3.66 (d, J=15.2 Hz, 1H), 3.60 (d, J=15.3 Hz, 1H), 2.17-2.31 (m, 1H), 2.02-2.13 (m, 1H), 2.07 (s, 3H), 1.47-1.65 (m, 1H), 0.95 (d, J=6.7 Hz, 3H), and 0.92 (d, J=6.7 Hz, 3H).

Example 8

-continued

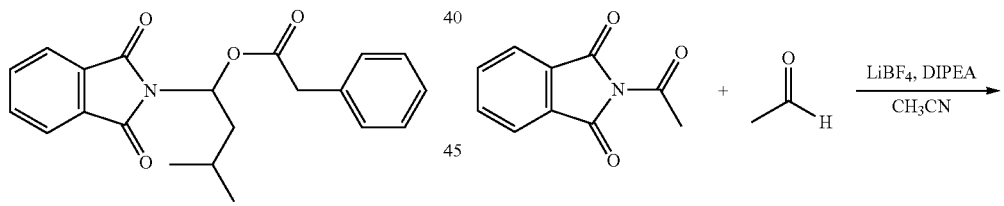

Spectral Data for the Product of Example 8: $^1$H NMR (300 MHz, CDCl$_3$, mixture of diastereomers): δ 7.85-7.91 (m, 2H), 7.72-7.79 (m, 2H), 6.68 (dd, J=6.5, 7.5 Hz, 1H), 4.97-5.07 (m, 1H), 2.45-2.56 (m, 2.25-2.37 (m), 2.07 (s, 3H), 1.83-2.15 (m), 1.55-1.61 (m, 6H), 1.14-1.70 (m), 0.98 (d, J=6.4 Hz, 3H, diastereomer-a), and 0.95 (d, J=6.5 Hz, 3H, diastereomer-b).

Example 9

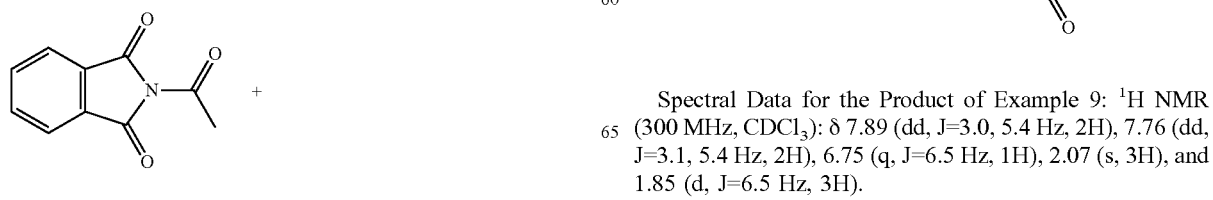

Spectral Data for the Product of Example 9: $^1$H NMR (300 MHz, CDCl$_3$): δ 7.89 (dd, J=3.0, 5.4 Hz, 2H), 7.76 (dd, J=3.1, 5.4 Hz, 2H), 6.75 (q, J=6.5 Hz, 1H), 2.07 (s, 3H), and 1.85 (d, J=6.5 Hz, 3H).

Example 10
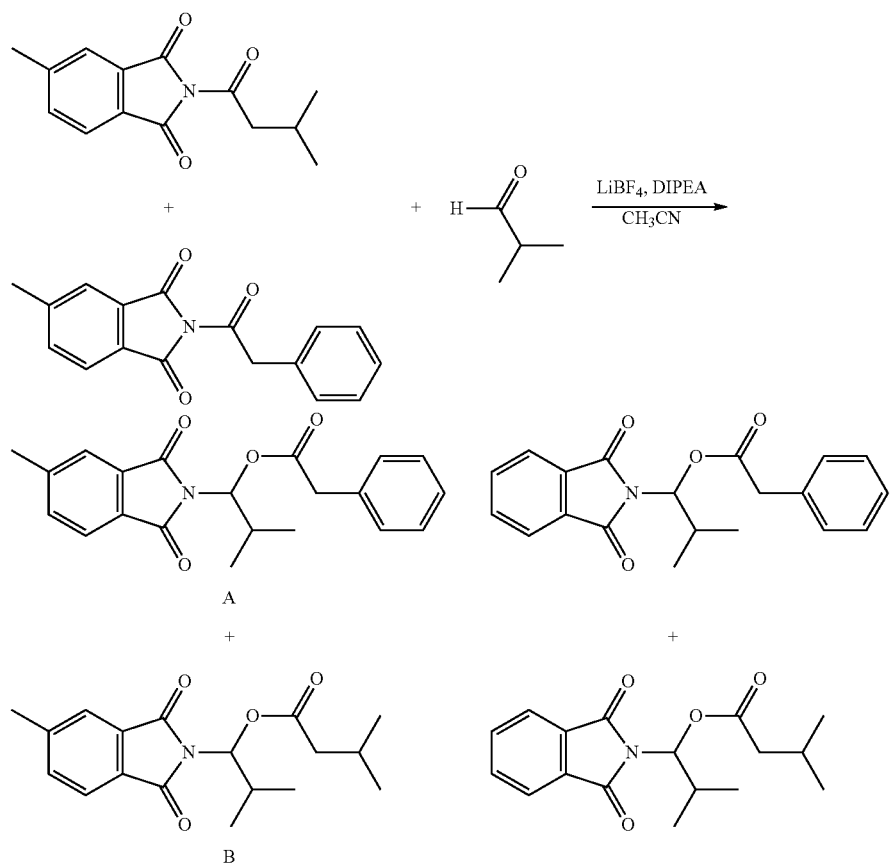
Spectral Data for Example 10-A: HR ESI-MS: $[C_{21}H_{21}NO_4+Na]^+$ requires 374.1363. Found 374.1364.
Spectral Data for Example 10-B: HR ESI-MS: $[C_{18}H_{23}NO_4+Na]^+$ requires 340.1519. Found 340.1521.
Example 11
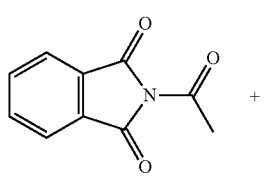
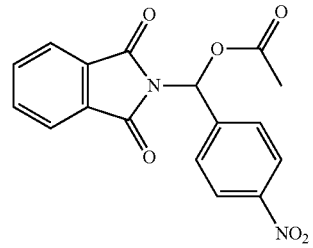
Spectral Data for the Product of Example 11: $^1$H NMR (300 MHz, CDCl$_3$): δ 8.25 (br d, J=8.7 Hz, 2H), 7.89 (dd, J=3.1, 5.4 Hz, 2H), 7.79 (dd, J=3.1, 5.4 Hz, 2H), 7.748 (br d, J=8 Hz, 2H), 7.737 (s, 1H), and 2.25 (s, 3H).
Example 12
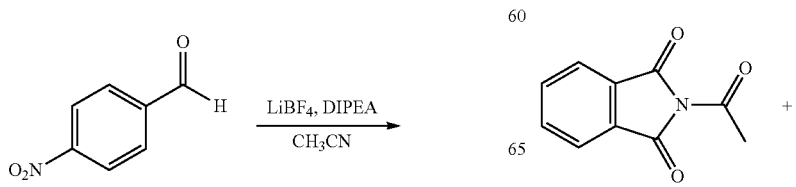

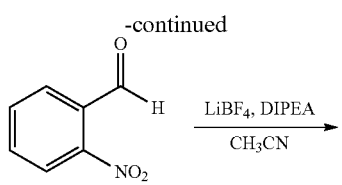

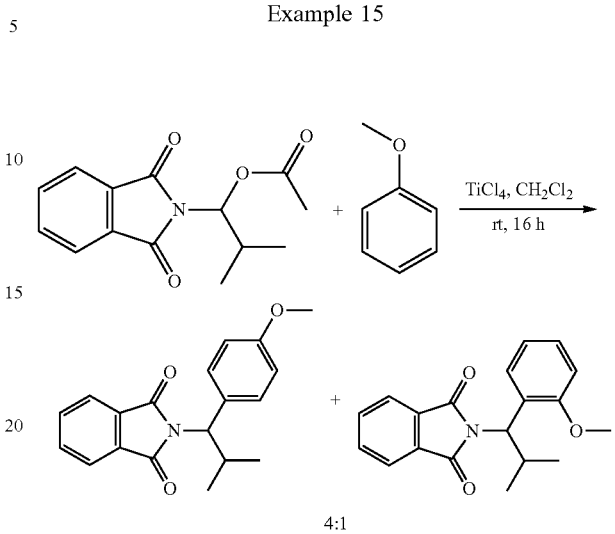

Spectral Data for the Product of Example 12: $^1$H NMR (300 MHz, CDCl$_3$): δ 8.20 (s, 1H), 8.25 (dd, J=1.2, 8.1 Hz, 1H), 7.96 (br d, J=8 Hz, 1H), 7.87 (dd, J=3.1, 5.4 Hz, 2H), 7.76 (dd, J=3.1, 5.6 Hz, 2H), 7.73 (ddd, J=1.3, 7.7, 7.7 Hz, 2H), 7.56 (ddd, J=1.4, 7.6, 8 Hz, 2H), and 2.19 (s, 3H).

Example 13

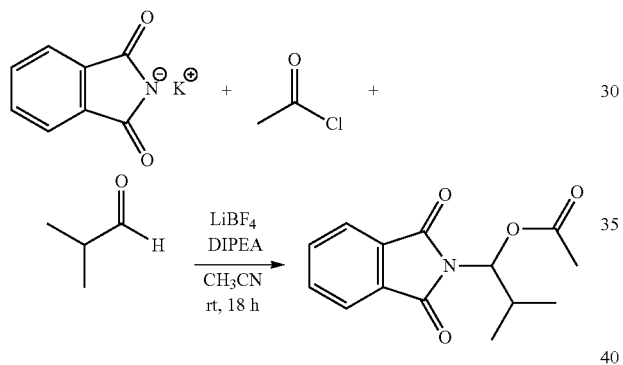

Spectral Data for the Product of Example 13: Identical to the spectral data for Example 2

Example 14

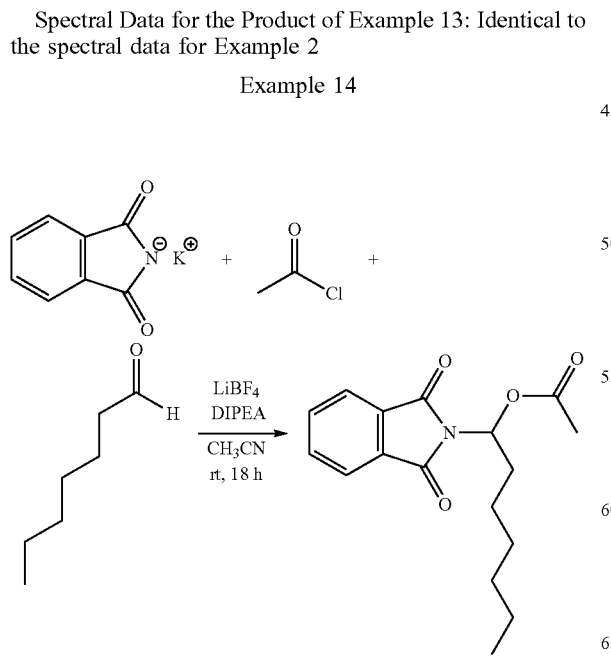

Spectral Data for the Product of Example 14: Identical to the spectral data for Example 3

Example 15

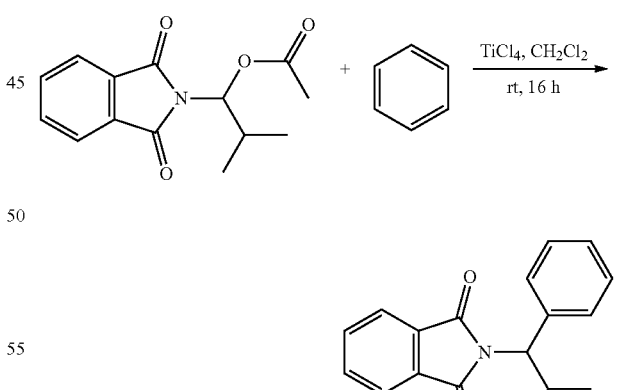

Spectral Data for the Major Product of Example 15: $^1$H NMR (300 MHz, CDCl$_3$, major isomer only): δ 7.78 (dd, J=3.1, 5.2 Hz, 2H), 7.66 (dd, J=3.0, 5.5 Hz, 2H), 7.53 (br d, J=8.7 Hz, 2H), 6.85 (br d, J=8.5 Hz, 2H), 4.78 (d, J=11.6 Hz, 1H), 3.77 (s, 3H), 3.21 (d sept, J=11.5, 6.7 Hz, 1H), 0.98 (d, J=6.5 Hz, 3H), and 0.87 (d, J=6.6 Hz, 3H). HR ESI-MS: [C$_{19}$H$_{19}$NO$_3$+Na]$^+$ requires 332.1257. Found 332.1257.

Spectral Data for Minor Isomer of Example 15: HR ESI-MS: [C$_{19}$H$_{19}$NO$_3$+Na]$^+$ requires 332.1257. Found 332.1255.

Example 16

Spectral Data for the Product of Example 16: $^1$H NMR (300 MHz, CDCl$_3$): δ 7.78 (dd, J=3.0, 5.4 Hz, 2H), 7.66 (dd, J=3.0, 5.4 Hz, 2H), 7.59-7.64 (m, 2H), 7.22-7.37 (m, 2H), 4.82 (d, J=11.6 Hz, 1H), 3.26 (d sept, J=11.6, 6.6 Hz, 1H), 2.07 (s, 3H), 1.00 (d, J=6.5 Hz, 3H), and 0.88 (d, J=6.6 Hz, 3H). HR ESI-MS: [C$_{18}$H$_{17}$NO$_2$+Na]$^+$ requires 302.1151. Found 302.1152.

Example 17

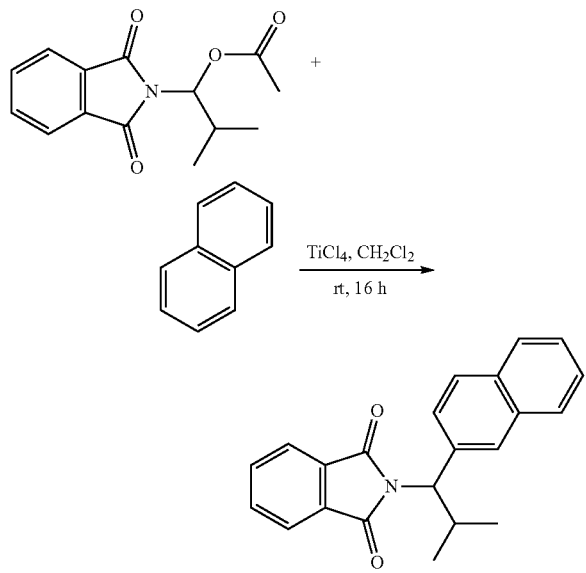

Spectral Data for the Product of Example 17: Found 302.1152. HR ESI-MS: $[C_{22}H_{19}NO_2+Na]^+$ requires 352.1308. Found 352.1310.

Example 18

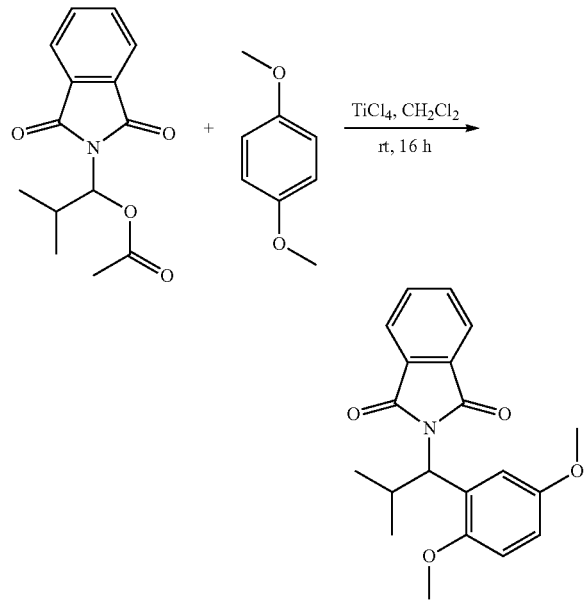

Spectral Data for the Product of Example 18: $^1$H NMR (300 MHz, CDCl$_3$): δ 7.79 (dd, J=3.1, 5.6 Hz, 2H), 7.67 (dd, J=3.2, 5.5 Hz, 2H), 7.50 (dd, J=1.1, 2.4 Hz, 1H), 6.78 (br d, J=2 Hz, 2H), 5.44 (d, J=11.6 Hz, 1H), 3.790 (s, 3H), 3.786 (s, 3H), 3.09 (d sept, J=11.6, 6.6 Hz, 1H), 0.99 (d, J=6.5 Hz, 3H), and 0.91 (d, J=6.6 Hz, 3H). HR ESI-MS: $[C_{20}H_{21}NO_4+Na]^+$ requires 362.1363. Found 362.1363.

Example 19

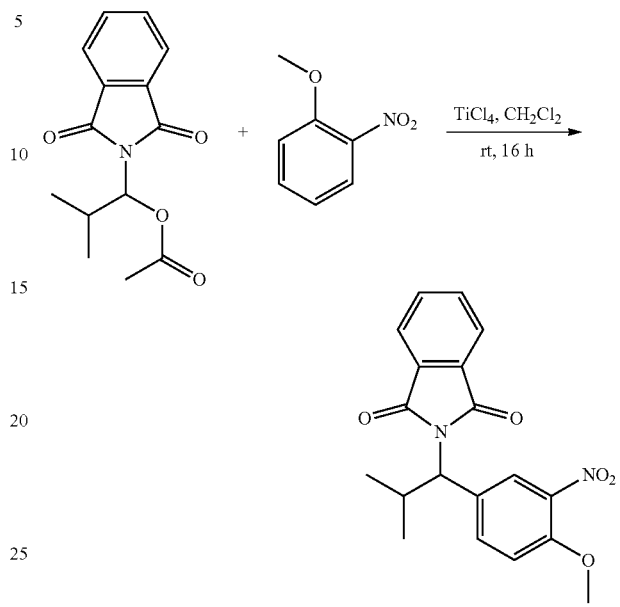

Spectral Data for the Product of Example 19: $^1$H NMR (300 MHz, CDCl$_3$): δ 8.09 (d, J=2.2 Hz, 2H), 7.82 (dd, J=3, 5.4 Hz, 2H), 7.81 (dd, J=8.6 Hz, 1H), 7.71 (dd, J=3.1, 5.5 Hz, 2H), 7.04 (d, J=8.7 Hz, 1H), 4.82 (d, J=11.6 Hz, 1H), 3.94 (s, 3H), 3.19 (d sept, J=11.6, 6.6 Hz, 1H), 0.99 (d, J=6.5 Hz, 3H), and 0.89 (d, J=6.6 Hz, 3H). HR ESI-MS: $[C_{19}H_{18}N_2O_5+Na]^+$ requires 377.1108. Found 377.1107.

Example 20

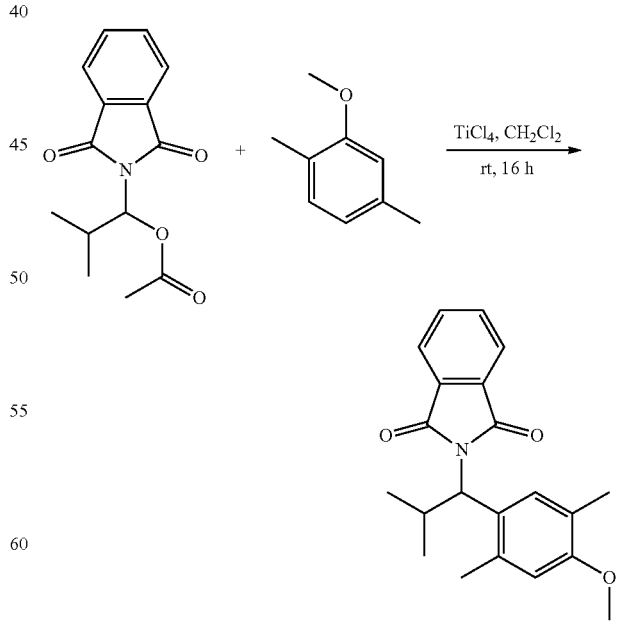

Spectral Data for the Product of Example 20: $^1$H NMR (300 MHz, CDCl$_3$): δ 7.78 (dd, J=3.1, 5.7 Hz, 2H), 7.67 (dd, J=3.2, 5.5 Hz, 2H), 7.57 (s, 1H), 6.57 (s, 1H), 5.06 (d, J=11.5

Hz, 1H), 3.87 (s, 3H), 3.18 (d sept, J=11.5, 6.5 Hz, 1H), 2.47 (s, 3H), 2.19 (s, 3H), 0.99 (d, J=6.5 Hz, 3H), and 0.85 (d, J=6.6 Hz, 3H). HR ESI-MS: [C$_{21}$H$_{23}$NO$_3$+Na]$^+$ requires 360.1570. Found 360.1569.

Example 21

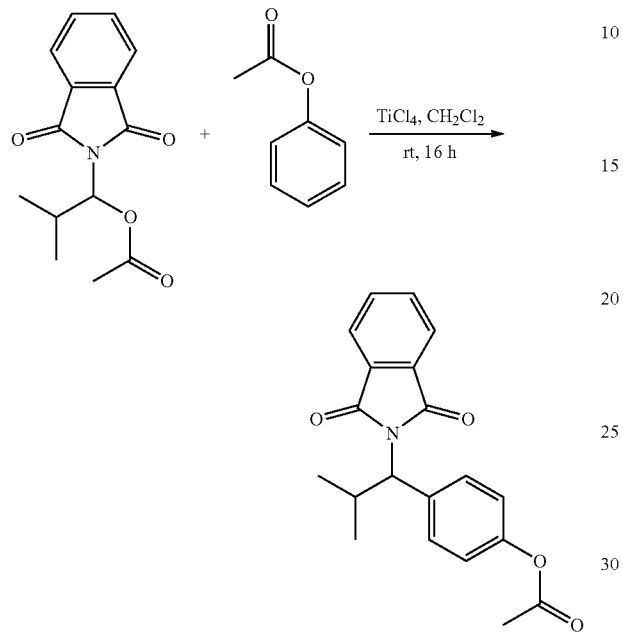

Spectral Data for the Product of Example 21: $^1$H NMR (300 MHz, CDCl$_3$): δ 7.75 (dd, J=2.9, 5.4 Hz, 2H), 7.56 (dd, J=2.9, 5.3 Hz, 2H), 7.45 (br d, J=8.5, 2H), 7.05 (br d, J=7, 2H), 4.77 (d, J=11.6 Hz, 1H), 3.17 (d sept, J=11.7, 6.5 Hz, 1H), 2.28 (s, 3H), 0.96 (d, J=6.5 Hz, 3H), and 0.84 (d, J=6.6 Hz, 3H).

Example 22

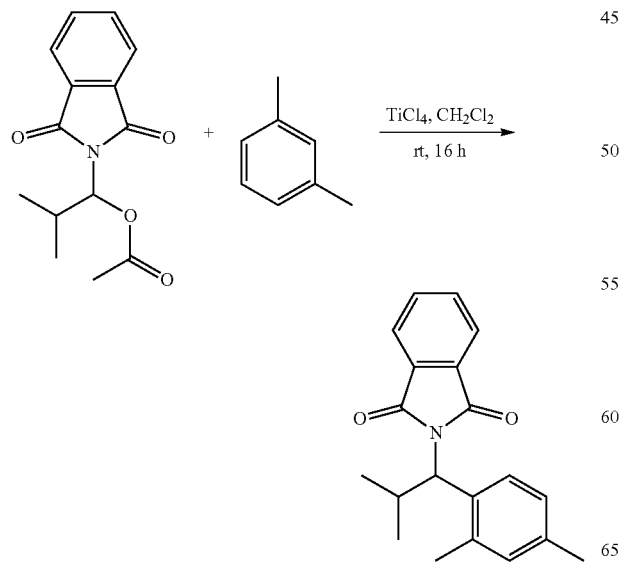

Spectral Data for the Product of Example 22: $^1$H NMR (300 MHz, CDCl$_3$): δ 7.85 (d, J=8.0 Hz, 1H), 7.78 (dd, J=3.0, 5.6 Hz, 2H), 7.66 (dd, J=3.3, 5.5 Hz, 2H), 7.03 (dd, J=2.1, 8.0 Hz, 1H), 1.00 (d, J=2.0 Hz, 1H), 5.11 (d, J=11.5 Hz, 1H), 3.20 (d sept, J=11.4, 6.6 Hz, 1H), 2.45 (s, 3H), 2.27 (s, 3H), 1.00 (d, J=6.5 Hz, 3H), and 0.86 (d, J=6.6 Hz, 3H). HR ESI-MS: [C$_{20}$H$_{21}$NO$_2$+Na]$^+$ requires 330.1465. Found 330.1466.

Example 23

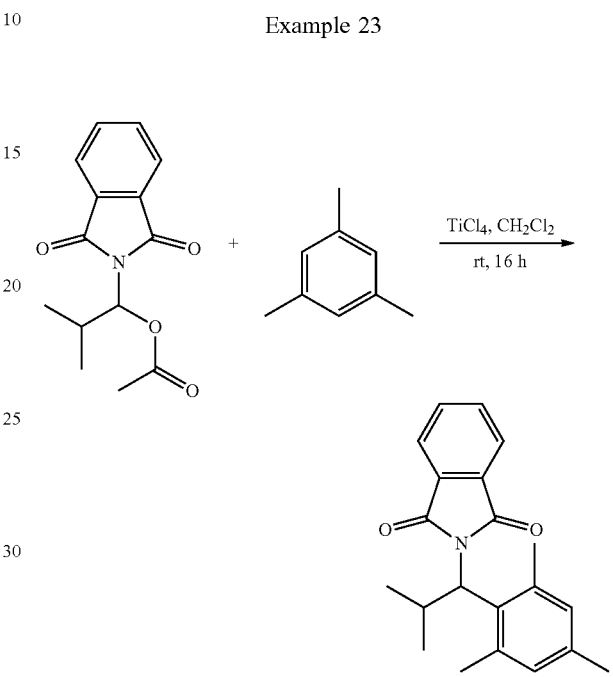

Spectral Data for the Product of Example 23: $^1$H NMR (300 MHz, CDCl$_3$): δ 7.76 (dd, J=3.1, 5.5 Hz, 2H), 7.67 (dd, J=3.1, 5.4 Hz, 2H), 6.81 (s, 2H), 5.20 (d, J=11.7 Hz, 1H), 3.54 (d sept, J=11.8, 6.6 Hz, 1H), 2.28 (s, 6H), 1.11 (d, J=6.1 Hz, 3H), and 0.79 (d, J=6.9 Hz, 3H). HR ESI-MS: [C$_{21}$H$_{23}$NO$_2$+Na]$^+$ requires 344.1621. Found 344.1621.

Example 24

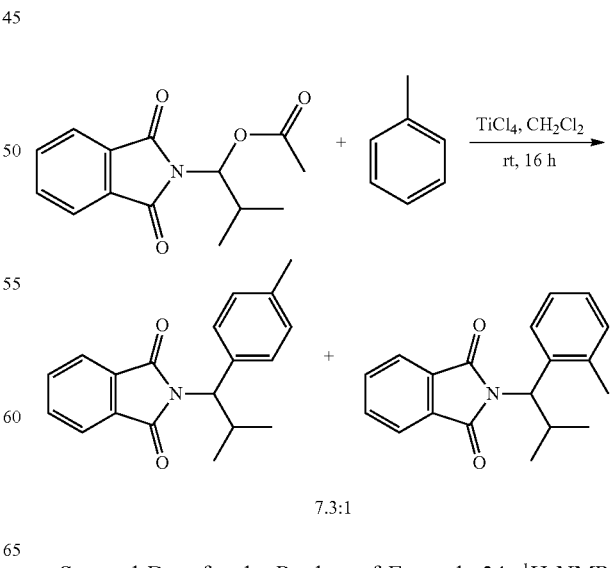

Spectral Data for the Product of Example 24: $^1$H NMR (300 MHz, CDCl$_3$, major isomer only): δ 7.77 (dd, J=3.1, 5.6 Hz, 2H), 7.65 (dd, J=3.0, 5.4 Hz, 2H), 7.51 (br d, J=8.1 Hz, 2H), 7.12 (br d, J=7.9 Hz, 2H), 4.80 (d, J=11.6 Hz, 1H), 3.24 (d sept, J=11.6, 6.6 Hz, 1H), 2.30 (s, 3H), 0.99 (d, J=6.5 Hz, 3H), and 0.88 (d, J=6.6 Hz, 3H). HR ESI-MS: $[C_{19}H_{19}NO_2+Na]^+$ requires 316.1308. Found 316.1307.

Example 25

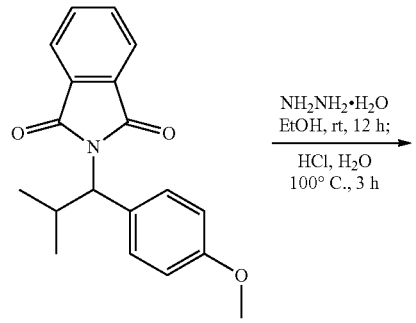

Spectral Data for the Product of Example 25: $^1$H NMR (300 MHz, CDCl$_3$): δ 7.21 (br d, J=8.6 Hz, 2H), 6.86 (br d, J=8.7 Hz, 2H), 3.80 (s, 3H), 3.56 (br d, J=7.1 Hz, 1H), 1.81 (ap octet, J=6.8 Hz, 1H), 0.97 (d, J=6.6 Hz, 3H), and 0.75 (d, J=6.7 Hz, 3H).

Example 26

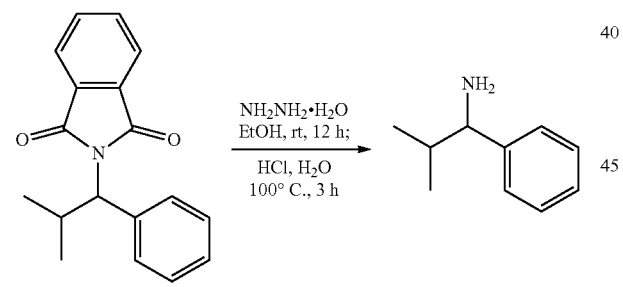

Spectral Data for the Product of Example 26: $^1$H NMR (300 MHz, CDCl$_3$): δ 7.20-7.35 (m, 5H), 3.63 (br d, J=7.4 Hz, 1H), 1.83-1.96 (m, 1H), 0.99 (d, J=6.7 Hz, 3H), and 0.77 (d, J=6.7 Hz, 3H).

Example 27

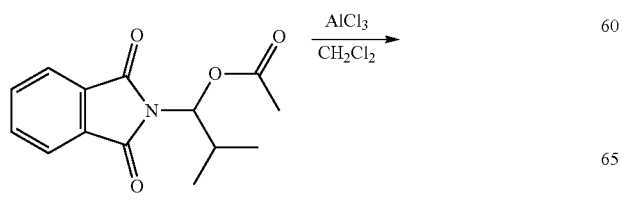

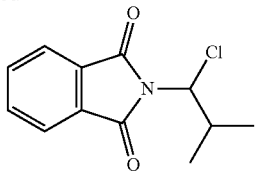

Spectral Data for the Product of Example 27: $^1$H NMR (300 MHz, CDCl$_3$): δ 7.91 (dd, J=3.1, 5.6 Hz, 2H), 7.78 (dd, J=3.1, 5.5 Hz, 2H), 5.67 (d, J=10.8 Hz, 1H), 3.12 (d sept, J=10.7, 6.7 Hz, 1H), 1.23 (d, J=6.6 Hz, 3H), and 0.91 (d, J=6.8 Hz, 3H).

Example 28

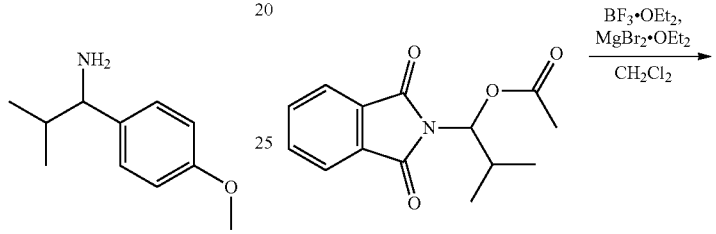

Spectral Data for the Product of Example 28: $^1$H NMR (300 MHz, CDCl$_3$): δ 7.91 (dd, J=3.2, 5.6 Hz, 2H), 7.78 (dd, J=3.1, 5.5 Hz, 2H), 5.82 (d, J=10.9 Hz, 1H), 3.19 (d sept, J=10.5, 6.9 Hz, 1H), 1.23 (d, J=6.6 Hz, 3H), and 0.92 (d, J=6.7 Hz, 3H).

Example 29

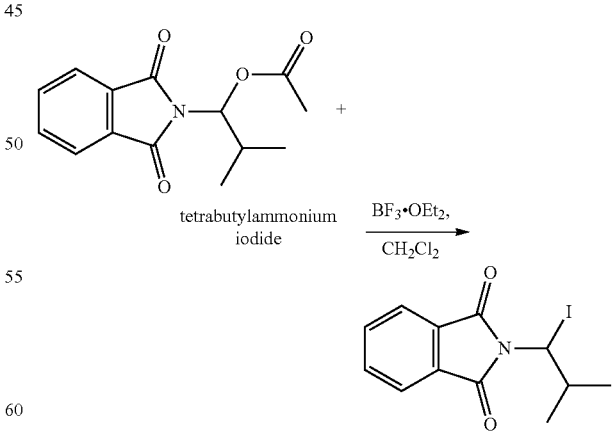

Spectral Data for the Product of Example 29: $^1$H NMR (300 MHz, CDCl$_3$): δ 7.90 (dd, J=3.1, 5.5 Hz, 2H), 7.78 (dd, J=3.1, 5.4 Hz, 2H), 6.03 (d, J=10.9 Hz, 1H), 3.09 (d sept, J=10.9, 6.9 Hz, 1H), 1.19 (d, J=6.6 Hz, 3H), and 0.89 (d, J=6.7 Hz, 3H).

Example 30

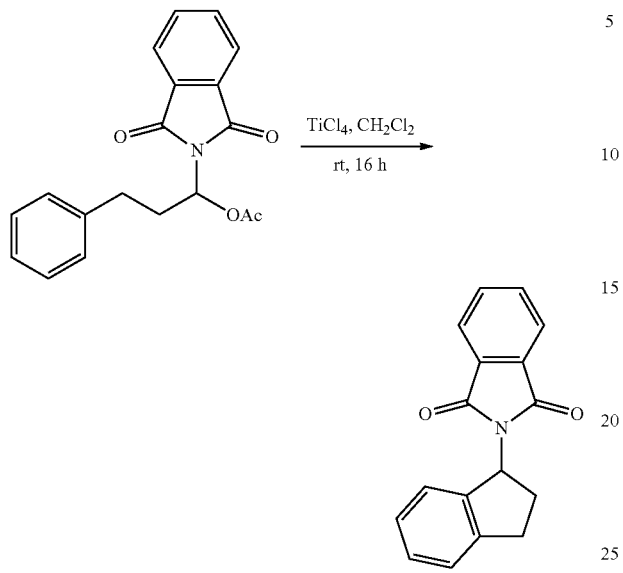

Spectral Data for the Product of Example 30: $^1$H NMR (300 MHz, CDCl$_3$): δ 7.82 (dd, J=3.1, 5.5 Hz, 2H), 7.71 (dd, J=3.1, 5.5 Hz, 2H), 7.07-7.33 (m, 4H), 5.88 (dd, J=6.4, 8.9 Hz, 1H), 3.38 (ddd sept, J=5.1, 8.8, 16.1 Hz, 1H), 2.94-3.06 (m, 1H), and 2.41-3.62 (m, 2H). HR ESI-MS: [C$_{17}$H$_{13}$NO$_2$+Na]$^+$ requires 286.0838. Found 286.0837.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising converting a compound of formula 4a to a corresponding compound of formula 6a with a Lewis acid and optionally a halo source,

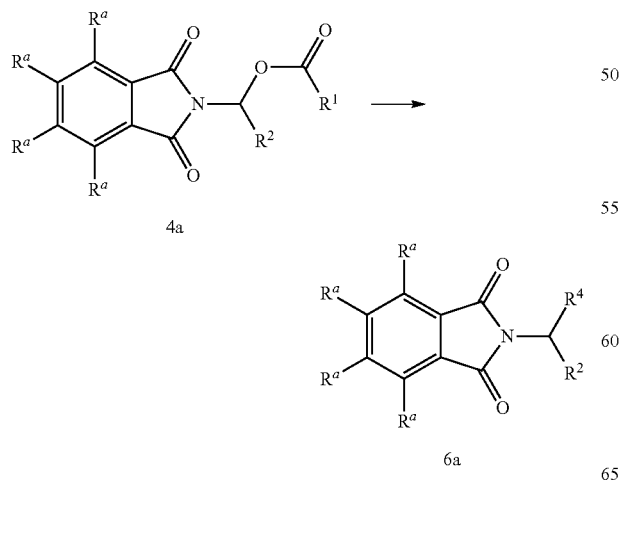

wherein:
R$^1$ is (C$_1$-C$_{10}$)alkyl, (C$_2$-C$_{10}$)alkenyl or (C$_2$-C$_{10}$)alkynyl wherein any (C$_1$-C$_{10}$)alkyl, (C$_2$-C$_{10}$)alkenyl, (C$_2$-C$_{10}$)alkynyl is optionally independently substituted with one or more phenyl or halo;
R$^2$ is (C$_1$-C$_{10}$)alkyl, (C$_2$-C$_{10}$)alkenyl, (C$_2$-C$_{10}$)alkynyl, or aryl wherein any (C$_1$-C$_{10}$)alkyl, (C$_2$-C$_{10}$)alkenyl, (C$_2$-C$_{10}$)alkynyl of R$^2$ is optionally substituted with one or more groups independently selected from halo, (C$_1$-C$_{10}$)alkoxy and aryl and wherein any aryl of R$^2$ is optionally substituted with one or more groups independently selected from halo, (C$_1$-C$_8$)alkyl, (C$_1$-C$_8$)alkoxy, nitro, and aryl; and
R$^4$ is a halo; and
each R$^a$ is independently selected from H, halo, (C$_1$-C$_6$)alkyl, (C$_2$-C$_6$)alkenyl, (C$_2$-C$_6$)alkynyl and (C$_1$-C$_6$)alkoxy wherein any (C$_1$-C$_6$)alkyl, (C$_2$-C$_6$)alkenyl, (C$_2$-C$_6$)alkynyl and (C$_1$-C$_6$)alkoxy is optionally independently substituted with one or more halo.

2. The method of claim 1 comprising converting the compound 4a to the corresponding compound 6a with titanium tetrachloride, boron trifluoride, trimethylsilyl trifluoromethanesulfonate, or silver trifluoromethanesulfonate in the presence of chlorotrimethylsilane.

3. The method of claim 1 comprising converting the compound 4a to the corresponding compound 6a with a Lewis acid and a halo source.

4. The method of claim 3 wherein the halo source is an ammonium halide, aluminum trihalide, boron trihalide, indium trihalide, or gallium trihalide.

5. The method of claim 1 comprising converting the compound 4a to the corresponding compound 6a with aluminum trichloride or borontrifluoro etherate, and optionally a halo source selected from tetrabutyl ammonim iodide and magnesium bromide.

6. The method of claim 1, wherein the compound of formula 4a has the following structure:

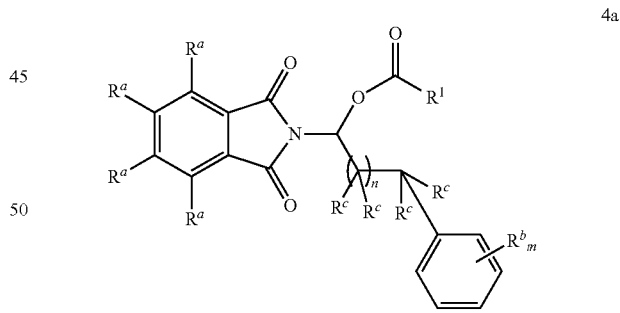

wherein:
R$^1$ is (C$_1$-C$_{10}$)alkyl, (C$_2$-C$_{10}$)alkenyl or (C$_2$-C$_{10}$)alkynyl wherein any (C$_1$-C$_{10}$)alkyl, (C$_2$-C$_{10}$)alkenyl, (C$_2$-C$_{10}$)alkynyl is optionally independently substituted with one or more phenyl or halo;
each R$^a$ is independently selected from H, halo, (C$_1$-C$_6$)alkyl, (C$_2$-C$_6$)alkenyl, (C$_2$-C$_6$)alkynyl and (C$_1$-C$_6$)alkoxy wherein any (C$_1$-C$_6$)alkyl, (C$_2$-C$_6$)alkenyl, (C$_2$-C$_6$)alkynyl and (C$_1$-C$_6$)alkoxy is optionally independently substituted with one or more halo;
each R$^b$ is independently selected from halo, (C$_1$-C$_6$)alkyl and (C$_1$-C$_6$)alkoxy;

m is 0, 1, 2, 3 or 4;

each $R^c$ is independently selected from H or methyl; and n is 1, 2 or 3.

7. The method of claim 1 further comprising preparing the compound of formula 4a by:

(a) reacting a corresponding salt of formula 1a with a corresponding compound of formula 2a and a corresponding aldehyde of formula 3 in the presence of a suitable Lewis acid,

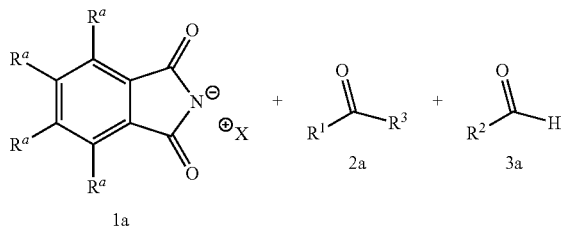

to provide the compound of formula 4a; or (b) reacting a corresponding compound of formula 5a, with an aldehyde of formula 3

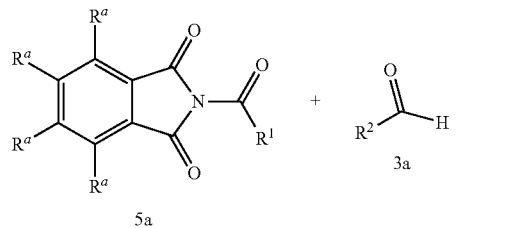

to provide the compound of formula 4a;

wherein:

X is a suitable counter ion; and $R^3$ is chloro, fluoro, bromo, cyano, or $(C_1-C_6)$alkanoyl, that is optionally substituted with one or more halo.

8. The method of claim 7 wherein X is sodium or potassium.

9. The method of claim 7 wherein each $R^a$ is H.

10. The method of claim 7 wherein $R^1$ is $(C_1-C_{10})$alkyl.

11. The method of claim 7 wherein the compound 2a is added to a mixture of a potassium salt of 1a, aldehyde 3a, LiBF$_4$, and triethylamine in acetonitrile to provide the compound of formula 4a.

12. A method for preparing an α-aryl phthalimide of formula 8a, wherein:

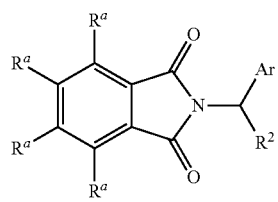

comprising treating a corresponding compound of formula 7a:

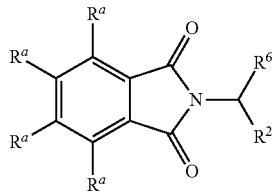

with an aromatic ring Ar and a suitable Lewis or Brønsted acid in a suitable solvent to provide the α-aryl phthalimide 8a, wherein:

$R^2$ is $(C_1-C_{10})$alkyl, $(C_2-C_{10})$alkenyl, $(C_2-C_{10})$alkynyl, or aryl wherein any $(C_1-C_{10})$alkyl, $(C_2-C_{10})$alkenyl, $(C_2-C_{10})$alkynyl of $R^2$ is optionally substituted with one or more groups independently selected from halo, $(C_1-C_{10})$alkoxy and aryl and wherein any aryl of $R^2$ is optionally substituted with one or more groups independently selected from halo, $(C_1-C_8)$alkyl, $(C_1-C_8)$alkoxy, nitro, and aryl;

$R^6$ is a —OC(=O)$R^1$ or halo;

Ar is a hydrocarbon aromatic ring that is optionally substituted with one or more groups independently selected from halo, nitro, $(C_1-C_6)$alkyl, $(C_2-C_6)$alkenyl, $(C_2-C_6)$alkynyl, $(C_1-C_6)$alkoxy and $(C_2-C_6)$alkanoyloxy, wherein any $(C_1-C_6)$alkyl, $(C_2-C_6)$alkenyl, $(C_2-C_6)$alkynyl, $(C_1-C_6)$alkoxy and $(C_2-C_6)$alkanoyloxy is optionally substituted with one or more halo;

$R^1$ is $(C_1-C_{10})$alkyl, $(C_2-C_{10})$alkenyl or $(C_2-C_{10})$alkynyl wherein any $(C_1-C_{10})$alkyl, $(C_2-C_{10})$alkenyl, $(C_2-C_{10})$alkynyl is optionally independently substituted with one or more phenyl or halo; and each $R^a$ is independently selected from H, halo, $(C_1-C_6)$alkyl, $(C_2-C_6)$alkenyl, $(C_2-C_6)$alkynyl and $(C_1-C_6)$alkoxy wherein any $(C_1-C_6)$alkyl, $(C_2-C_6)$alkenyl, $(C_2-C_6)$alkynyl and $(C_1-C_6)$alkoxy is optionally independently substituted with one or more halo.

13. The method of claim 12 wherein $R^a$ is H.

14. The method of claim 12 wherein $R^1$ is $(C_1-C_{10})$alkyl.

15. The method of claim 12 wherein the suitable reagent comprises a Lewis acid or Bronsted acid selected from the group consisting of titanium tetrachloride, trimethylsilyl trifluoromethanesulfonate, a combination of chlorotrimethylsilane and silver(I) trifluoromethanesulfonate, trifluoromethanesulfonic acid, tetrafluoroboric acid, trifluoromethanesulfonimide, a phosphoric acid, a phosphoramide, and a disulfonylimide.

16. The method of claim 12 wherein the treating is carried out in the presence of a chiral phase transfer catalyst selected from a chiral phosphoric acid conjugate base and a chiral borate.

17. The method of claim 12 further comprising treating the α-aryl phthalimide 8a under suitable conditions to provide the corresponding α-branched aryl amine 9a:

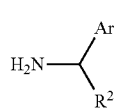

or a salt thereof.

18. The method of claim 17 wherein the conditions comprise treatment with hydrazine hydrate.

\* \* \* \* \*

UNITED STATES PATENT AND TRADEMARK OFFICE
CERTIFICATE OF CORRECTION

PATENT NO. : 9,701,633 B2  
APPLICATION NO. : 14/989628  
DATED : July 11, 2017  
INVENTOR(S) : Patrick H. Willoughby et al.

Page 1 of 1

It is certified that error appears in the above-identified patent and that said Letters Patent is hereby corrected as shown below:

In the Claims

Column 39, Line 25, Claim 7, please delete "with an aldehyde of formula 3" and insert -- with an aldehyde of formula 3a; -- therefor.

Signed and Sealed this  
Twenty-first Day of November, 2017

Joseph Matal  
*Performing the Functions and Duties of the*  
*Under Secretary of Commerce for Intellectual Property and*  
*Director of the United States Patent and Trademark Office*